Figure 1:
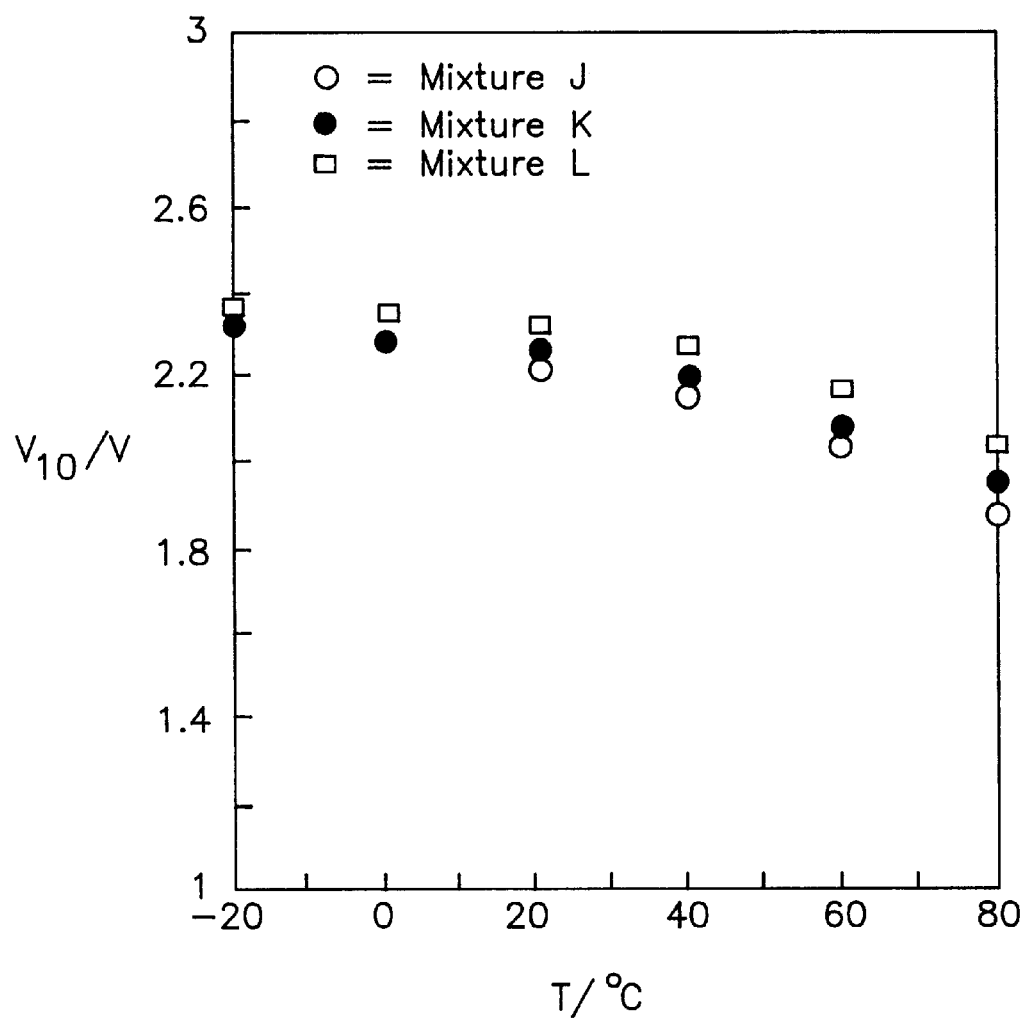
Figure 2:
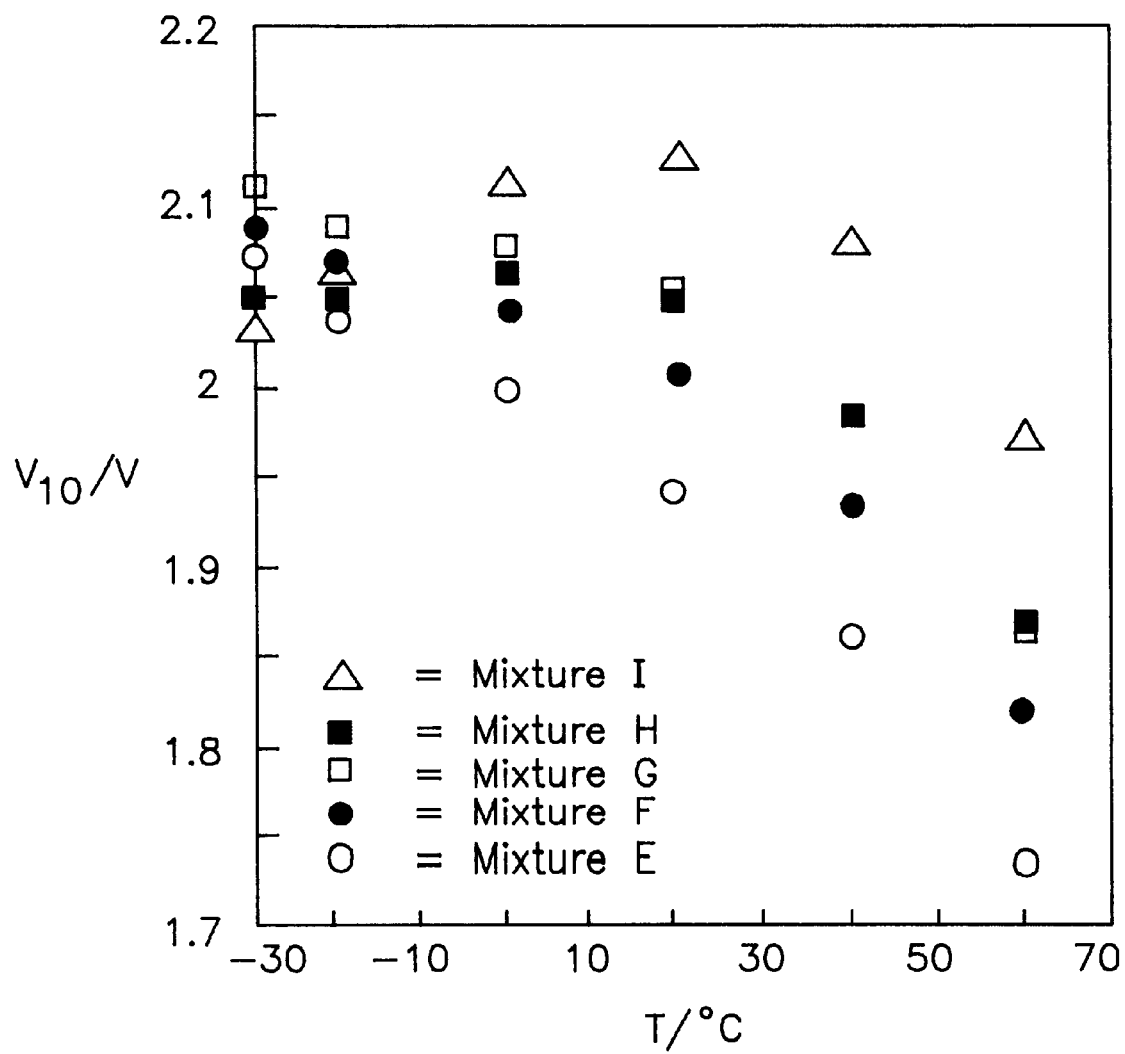
Figure 3:
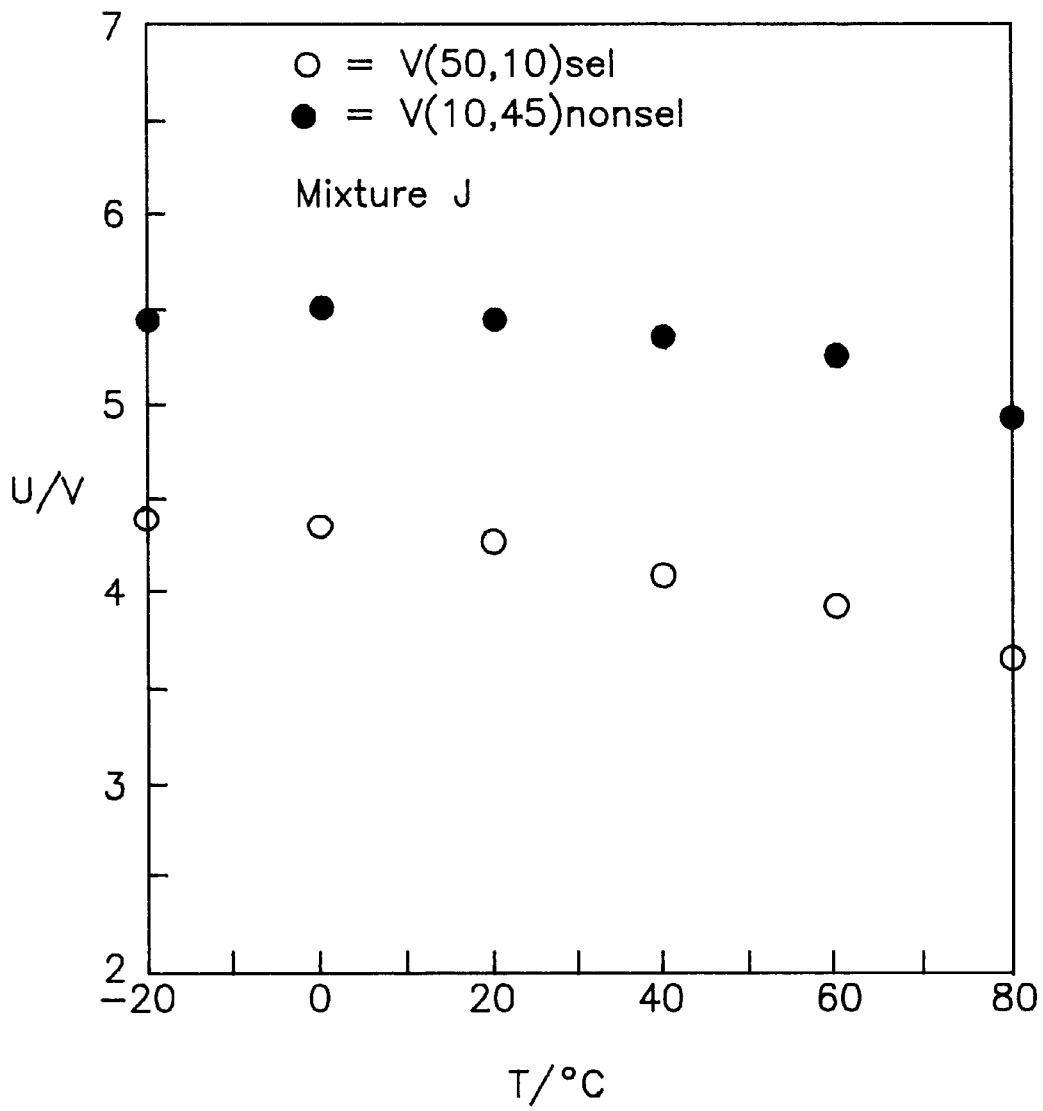
Figure 4:
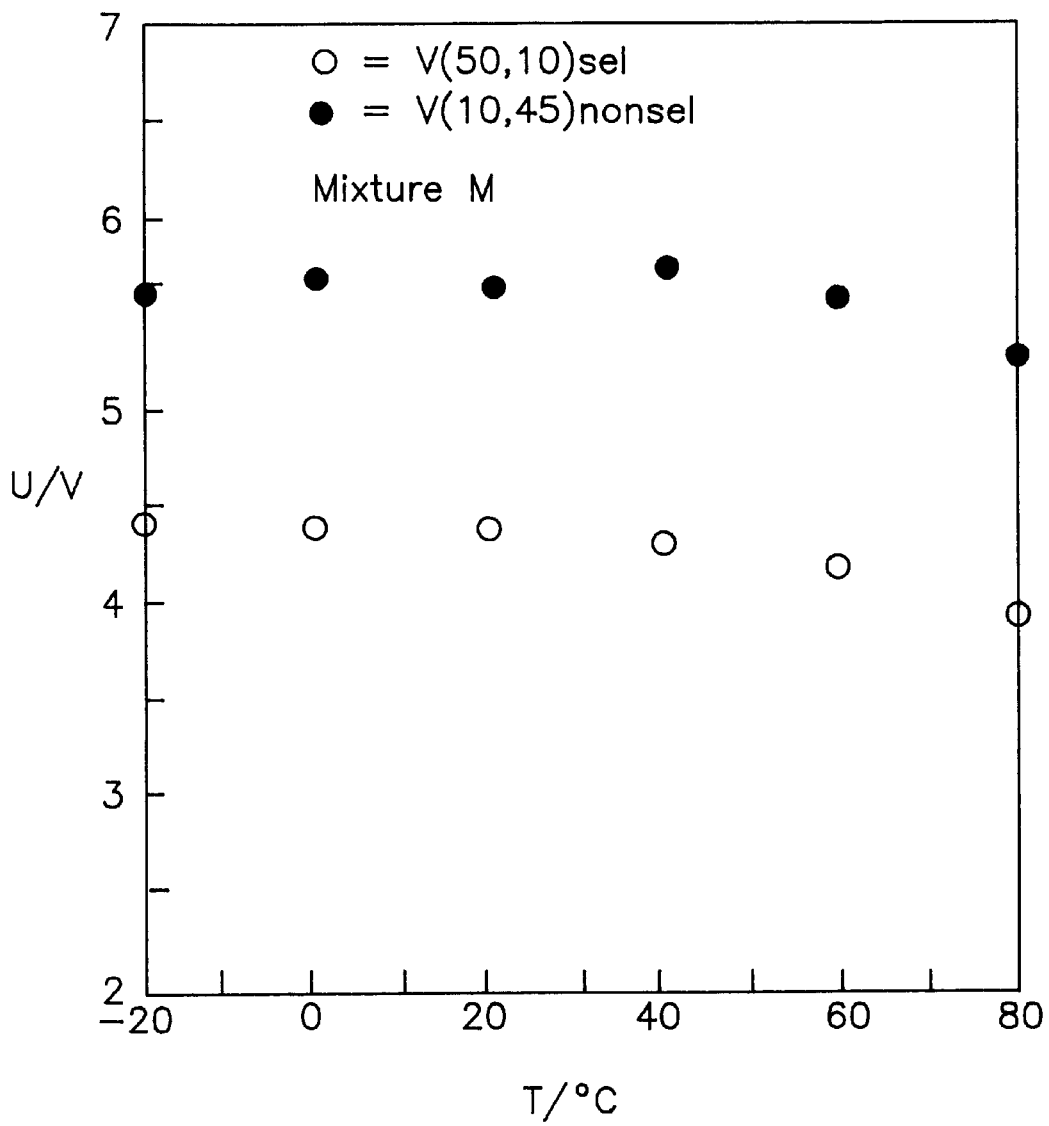

United States Patent [19]
Reiffenrath et al.

[11] Patent Number: 6,056,893
[45] Date of Patent: *May 2, 2000

[54] DOPANTS

[75] Inventors: Volker Reiffenrath, Rossdorf; Georg Weber, Erzhausen, both of Germany

[73] Assignee: Merck Patent Gesellschaft mit Beschrankter Haftung, Germany

[*] Notice: This patent is subject to a terminal disclaimer.

[21] Appl. No.: 08/961,559

[22] Filed: Oct. 30, 1997

[30] Foreign Application Priority Data

Oct. 31, 1996 [DE] Germany .................. 196 44 043

[51] Int. Cl.⁷ .................. C09K 19/34; C09K 19/30; C09K 19/52; C09K 19/12
[52] U.S. Cl. .................. 252/299.6; 252/299.01; 252/299.61; 252/299.63; 252/299.62; 252/299.66; 568/626; 568/647
[58] Field of Search .................. 252/299.6, 299.61, 252/299.63, 299.66, 299.01, 299.62

[56] References Cited

U.S. PATENT DOCUMENTS 5,653,911 8/1997 Kondo et al. .................. 252/299.01
5,702,642 12/1997 Yamada et al. .................. 252/299.66
5,709,911 1/1998 Onishi et al. .................. 428/1

*Primary Examiner*—C. H. Kelly
*Attorney, Agent, or Firm*—Miller, White, Zelano, & Branigan, P.C.

[57] ABSTRACT

A dopant compound of the formula I $$R^1-(A^1-Z^1)_n-A^2-W \qquad I$$

in which

W is 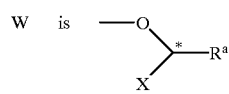

and $R^1$, $A^1$, $A^2$, $Z^1$ n, X and $R^a$ are as defined in claim 1, and to the use thereof as chiral dopants in liquid-crystalline media for electro-optical displays, and to electro-optical displays containing such media.

17 Claims, 4 Drawing Sheets

DOPANTS

The invention relates to dopants of the formula

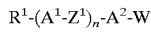

in which
W is

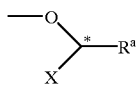

X is —C≡C—Y or —CH=CH—Y,

Y a) is H or an alkyl or alkenyl radical having 1–15 carbon atoms which is unsubstituted, monosubstituted by CN or $CF_3$ or at least monosubstituted by halogen, where one or more $CH_2$ groups in these radicals may also be replaced, in each case independently of one another, by —O—, —CO— or —CO—O— in such a way that heteroatoms are not linked directly to one another, or b) is a phenylene radical in which one or two CH groups may be replaced by N and which is unsubstituted or substituted by CN, Cl or F or by an alkyl, alkenyl or alkoxy radical having 1 to 8 carbon atoms, in which one or more H atoms may be replaced by F atoms, $R^a$ is a straight-chain alkyl radical having 1–15 carbon atoms, $R^1$ is H or an alkyl or alkenyl radical having 1–15 carbon atoms which is unsubstituted, monosubstituted by CN or $CF_3$ or at least monosubstituted by halogen, where one or more $CH_2$ groups in these radicals may also be replaced, in each case independently of one another, by —O—, —S—, —CO—, —CO—O—, —O—CO— or —O—CO—O— in such a way that heteroatoms are not linked directly to one another, $A^1$ and $A^2$, in each case independently of one another, are a a) trans-1,4-cyclohexylene radical, in which one or more nonadjacent $CH_2$ groups may also be replaced by —O— and/or —S—, b) 1,4-cyclohexenylene radical, c) 1,4-phenylene radical, in which one or two CH groups may also be replaced by N, d) radical from the group consisting of 1,4-bicyclo[2.2.2]octylene, piperidine-1,4-diyl, naphthalene-2,6-diyl, deca-hydronaphthalene-2,6-diyl and 1,2,3,4-tetrahydronaphthalene-2,6-diyl, where the radicals a), b) and c) may be substituted one or more times by CN, Cl, F or an alkyl or alkenyl radical having 1 to 5 carbon atoms, $Z^1$ is —CO—O—, —O—CO—, —$CH_2$O—, —O—$CH_2$—, —$CH_2CH_2$—, —CH=CH—, —C≡C— or a single bond, and n is 0, 1, 2 or 3, with the proviso that, in the case where $A^2$ is unsubstituted 1,4-phenylene and X is C≡CH, $A^1$ is not 1,4-phenylere in which one or two CH groups may also be replaced by N.

The use of the novel chiral compounds in nematic liquid-crystal mixtures allows the cholesteric pitch of the latter to be matched to the requirements of various applications. For example, a substantially temperature-independent cholesteric pitch can be obtained, for example, for "phase-change" displays having, for example, a field-induced phase change from cholesteric to nematic or in STN displays. However, it is likewise possible to achieve high temperature dependences of the cholesteric pitch, which can have either positive or negative values.

Since a negative temperature dependence of the cholesteric pitch results in a reduction in the pitch with rising temperature, and a reduction in the pitch results in an increase in the threshold or operating voltage in various electro-optical display elements, for example in TN displays, but also in STN displays, the use of the novel chiral substances in nematic liquid-crystal mixtures allows the otherwise predominant reduction in the threshold or operating voltage with increasing temperature to be virtually compensated. It is advantageous here to use a suitable mixing concept even without the novel dopants to establish a relatively low temperature dependence of the threshold. This simplifies addressing of such display elements.

In particular in the last decade, liquid crystals have been introduced into various industrial areas in which electro-optical and display-device properties are in demand (for example in watch, calculator and typewriter displays). These display devices are based on the dielectric alignment effects in the nematic, cholesteric and/or smectic phases of the liquid-crystalline compounds, where—caused by the dielectric anisotropy—the long molecular axis of the compounds adopts a preferential alignment in an applied electric field. The usual response times in these display devices are too loig for many other potential areas of application of liquid crystals. This disadvantage is particularly noticeable if a large number of pixels need to be addressed. The production costs for devices containing relatively large screen areas, for example video equipment, are then generally too high.

Besides nematic and cholesteric liquid crystals, optically active smectic liquid-crystal phases have also increasingly achieved importance over the last few years.

Clark and Lagerwall have been able to show that the use of ferroelectric liquid-crystal systems in very thin cells results in opto-electric switching or display elements which have response times which are faster by a factor of up to 1000 than conventional TN ("twisted nematic") cells (cf., for example, Lagerwall et al. "Ferroelectric Liquid Crystals for Displays", SID Symposium, October Meeting 1985, San Diego, Calif., USA). Owing to these and other favorable properties, for example the possibility of bi-stable switching and the fact that the contrast is virtually independent of the viewing angle, FLCs are in principle highly suitable for the abovementioned areas of application, for example via matrix addressing.

For electro-optical switching and display elements, there is a need either for compounds which form suitable or orthogonal smectic phases and are themselves optically active, or ferroelectric smectic phases can be induced by doping compounds which, although forming such smectic phases, are not themselves optically active, with optically active compounds. The desired phase should be stable over the largest possible temperature range.

In order to achieve a good contrast ratio in electro-optical devices, a uniform planar alignment of the liquid crystals is necessary. Good alignment in the $S^*_A$ and $S^*_C$ phase can be achieved if the phase sequence of the liquid-crystal mixture with decreasing temperature is as follows:

Isotropic→N*→$S^*_A$→$S^*_C$

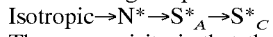

The prerequisite is that the pitch of the helix in the N* phase is very large (greater than 10 μm) or even better is fully compensated (see, for example, T. Matsumoto et al., p. 468–470, Proc. of the 6th Int. Display Research Conf., Japan Display, Sep. 30–Oct. 2, 1986, Tokyo, Japan; M. Murakami et al., ibid p. 344–p. 347). This is achieved by mixing the chiral liquid-crystal mixture which has, for example, a left-handed helix in the N* phase with a further optically active dopant which induces a right-handed helix in such amounts that the helix is just compensated.

It has been found that optically active compounds of the formula I as dopants in tilted smectic liquid-crystal phases result in very strong twisting in the cholesteric phase even when added in small amounts.

This helix induced in the N* phase can advantageously be used in mixtures for specific compensation of the pitch. It is particularly advantageous here that the novel dopants, owing to their high twisting power, compensate the pitch of another dopant even when added in small amounts.

JP-A 03 193 740 A2 discloses similar substituted alkynyl phenyl ethers and alkynyl benzoates which have optical activity.

In the pure state, the compounds of the formula I are colorless and frequently themselves form liquid-crystalline mesophases in a temperature range which is favorably located for electro-optical use. They are stable chemically, thermally and to light.

The invention thus relates to the compounds of the formula I and to the use of these compounds as components of liquid-crystalline media. The invention furthermore relates to liquid-crystalline media containing at least one compound of the formula I, and to liquid-crystal display elements, in particular electro-optical display elements, which contain media of this type.

Above and below, $R^1$, $A^1$, $Z^1$, n, $A^2$ and W are as defined above, unless expressly stated otherwise.

For reasons of simplicity, Cyc below denotes a 1,4-cyclohexylene radical, Che denotes a 1,4-cyclohexenylene radical, Dio denotes a 1,3-dioxane-2,5-diyl radical, Dit denotes a 1,3-dithiane-2,5-diyl radical, Phe denotes a 1,4-phenylene radical, Pyd denotes a pyridine-2,5-diyl radical, Pyr denotes a pyrimidine-2,5-diyl radical and Bco denotes a bicyclo[2.2.2]octylene radical, where Cyc and/or Phe may be unsubstituted or monosubstituted or polysubstituted by Cl, F or CN.

The compounds of the formula I include compounds containing a ring in the mesogenic group $R^1$-$(A^1$-$Z^1)_n$-$A^2$- of the subformula Ia:

$R^1$-$A^2$-W    Ia, compounds containing two rings in the mesogenic group $R^1$-$(A^1$-$Z^1)_n$-$A^2$- of the subformulae Ib to Ic:

$R^1$-$A^1$-$A^2$-W    Ib

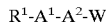

$R^1$-$A^1$-$Z^1$-$A^2$-W    Ic and compounds containing three rings in the mesogenic group $R^1$-$(A^1$-$Z^1)_n$-$A^2$- of the subformulae Id to Ig:

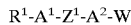

| | |
|---|---|
| $R^1$—$A^1$—$A^1$—$A^2$—W | Id |
| $R^1$—$A^1$—$Z^1$—$A^1$—$A^2$—W | Ie |
| $R^1$—$A^1$—$A^1$—$Z^1$—$A^2$—W | If |
| $R^1$—$A^1$—$Z^1$—$A^1$—$Z^1$—$A^2$—W | Ig |

Of these, particular preference is given to those of the subformulae Ia, Ib, Ic, Id, Ie and If.

The preferred compounds of the subformula Ia include those of the subformulae Iaa and Iab:

$R^1$-Phe-W    Iaa

$R^1$-Cyc-W    Iab

The preferred compounds of the subformula Ib include those of the subformulae Iba to Ibg:

| | |
|---|---|
| $R^1$—Cyc—Cyc—W | Iba |
| $R^1$—Cyc—Phe—W | Ibb |
| $R^1$—Phe—Phe—W | Ibc |
| $R^1$—Pyd—Phe—W | Ibd |
| $R^1$—Phe—Cyc—W | Ibe |
| $R^1$—Dio—Phe—W | Ibf |
| $R^1$—Pyr—Phe—W | Ibg |

Of these, those of the formulae Iba, Ibb, Ibc and Ibe are particularly preferred.

The preferred compounds of the subformula Ic include those of the subformulae Ica to Ich:

| | |
|---|---|
| $R^1$—Cyc—$Z^1$—Cyc—W | Ica |
| $R^1$—$A^1$—$CH_2CH_2$—$A^2$—W | Icb |
| $R^1$—Cyc—$Z^1$—Phe—W | Icc |
| $R^1$—$A^1$—OCO—Phe—W | Icd |
| $R^1$—Phe—$Z^1$—Phe—W | Ice |
| $R^1$—Pyr—$Z^1$—$A^2$—W | Icf |
| $R^1$—Pyd—$Z^1$—$A^2$—W | Icg |
| $R^1$—Dio—$Z^1$—$A^2$—W | Ich |

Of these, those of the subformulae Ica, Icb, Icc and Ice are particularly preferred.

The preferred compounds of the subformulae Id to Ig include those of the subformulae Ih to Io:

| | |
|---|---|
| $R^1$—$A^1$—Cyc—Cyc—W | Ih |
| $R^1$—$A^1$—Cyc—Phe—W | Ii |
| $R^1$—$A^1$—$CH_2CH_2$—$A^1$—Phe—W | Ij |
| $R^1$—Cyc—$Z^1$—$A^1$—$Z^1$—Phe—W | Ik |
| $R^1$—Phe—Phe—Phe—W | Il |
| $R^1$—Phe—$Z^1$—$A^1$—Phe—W | Im |
| $R^1$—$A^1$—Phe—$Z^1$—Phe—W | In |
| $R^1$—$A^1$—$Z^1$—Cyc—Phe—W | Io |

In the compounds of the formulae above and below, $R^1$ is preferably alkyl or alkenyl, furthermore preferably alkoxy.

$A^1$ and $A^2$, independently of one another, are preferably Phe, Cyc, Che, Pyd, Pyr or Dio. The compounds of the formula I preferably contain not more than one of the radicals Bco, Pyd, Pyr, Dio and Dit.

If two rings $A^1$ are present, they may have identical or different meanings. The same applies to the bridge $Z^1$.

Preference is also given to compounds of the formula I and of all subformulae in which $A^2$ is 1,4-phenylene which is monosubstituted or disubstituted by Cl and/or F.

$A^1$ and $A^2$ are preferably

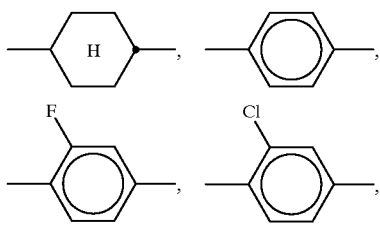

-continued

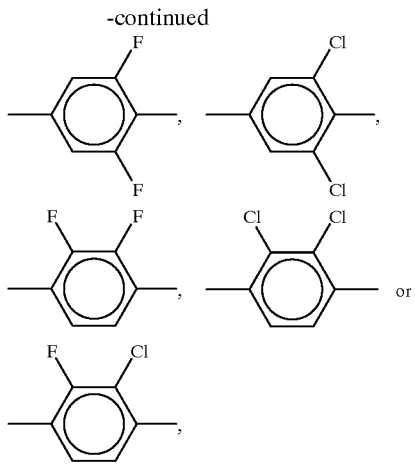

where the rings may also be present in inverted form.

$A^1$ is particularly preferably unsubstituted 1,4-cyclohexylene.

n is preferably 0, 1 or 2, particularly preferably 2. $Z^1$ is preferably —CH$_2$CH$_2$—, —CO—O—, —O—CO— or a single bond, particularly preferably a single bond.

In the structural units W, X is preferably —CH=CH$_2$, —C≡CH or

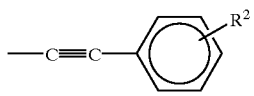

, in which $R^2$ is preferably CN, F or an alkyl or alkoxy radical having 1 to 8 carbon atoms, in which one or more H atoms may be replaced by F atoms. $R^2$ is in particular CN in the para-position to the alkynyl group. $R^a$ is preferably a straight-chain alkyl radical having 1–12 carbon atoms. $R^a$ is particularly preferably a straight-chain alkyl radical having 1–8 carbon atoms.

The formulae (1)–(3) show particularly preferred meanings of the structural unit W:

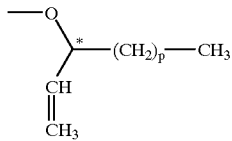  (1)

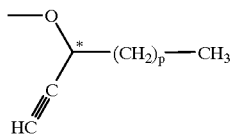  (2)

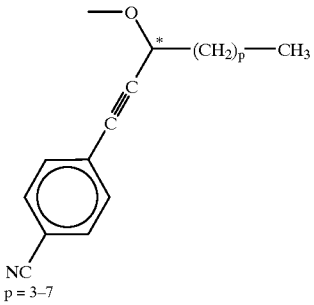  (3)

If $R^1$ in the formulae above and below is an alkyl radical and/or an alkoxy radical, this may be straight-chain or branched. It is preferably straight-chain, has 2,3,4,5,6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl.

If $R^1$ is an alkyl radical in which one CH$_2$ group has been replaced by —CH=CH—, this may be straight-chain or branched. It is preferably straight-chain and has 2 to 10 carbon atoms. Accordingly, it is in particular vinyl, prop-1- or prop-2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, dec-1-, -2-, -3-, -4-, -5-, -6-, -7-, -8- or -9-enyl.

If $R^1$ is an alkyl radical in which one CH$_2$ group has been replaced by —O— and one has been replaced by —CO—, these are preferably adjacent. These thus contain an acyloxy group —CO—O— or an oxycarbonyl group —O—CO—. These are preferably straight-chain and have 2 to 6 carbon atoms.

Accordingly, they are, in particular, acetyloxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxy-carbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl) ethyl, 2-(propoxycarbonyl) ethyl, 3-(methoxycarbonyl)propyl, 3-(ethoxycarbonyl)propyl, 4-(methoxycarbonyl)butyl.

If $R^1$ is an alkyl radical in which one CH$_2$ group has been replaced by unsubstituted or substituted —CH=CH—and an adjacent CH$_2$ group has been replaced by —CO— or —CO—O— or —O—CO—, this may be straight-chain or branched. It is preferably straight-chain and has 4 to 13 carbon atoms. Accordingly, it is in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexym, 7-methacryloyloxyheptyl, 8-methacryloyloxyoctyl or 9-methacryloyloxynonyl.

If $R^1$ is an alkyl or alkenyl radical which is monosubstituted by CN or $CF_3$, this radical is preferably straight-chain and the substitution by CN or $CF_3$ is in the ω-position.

If $R^1$ is an alkyl or alkenyl radical which is at least monosubstituted by halogen, this radical is preferably straight-chain and halogen is preferably F or Cl. In the case of multiple substitution, halogen is preferably F. The resultant radicals also include perfluorinated radicals. In the case of mono-substitution, the fluorine or chlorine substituent can be in any desired position, but is preferably in the ω-position.

Compounds of the formula I containing a branched wing group $R^1$ may occasionally be of importance owing to better solubility in the conventional liquid-crystalline base materials, in particular as chiral dopants if they are optically active. Smectic compounds of this type are suitable as components of ferroelectric materials.

Branched groups of this type generally contain not more than one chain branch. Preferred branched radicals $R^1$ are isopropyl, 2-butyl(=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy or 1-methylheptoxy.

In particular, $R^1$ is a straight-chain unsubstituted alkyl radical having 1 to 7 carbon atoms or a straight-chain unsubstituted alkenyl radical having 1 to 7 carbon atoms.

The formula I also includes the optical antipodes and mixtures thereof.

Of these compounds of the formula I and the subformulae, preference is given to those in which at least one of the radicals present therein has one of the preferred meanings indicated.

In the compounds of the formula I, preference is given to the stereoisomers in which the rings Cyc and piperidine are trans-1,4-disubstituted. Those of the above formulae which contain one or more groups Pyd, Pyr and/or Dio in each case include both 2,5-positional isomers.

Some very particularly preferred subgenera of compounds of the formula I are those of the subformulae I1 to I6:

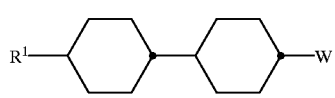

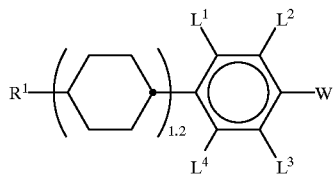

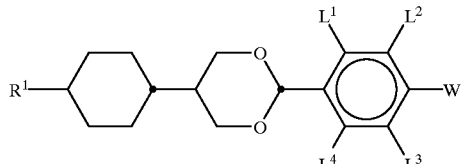

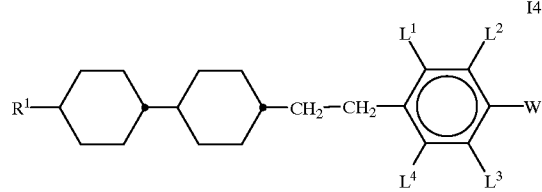

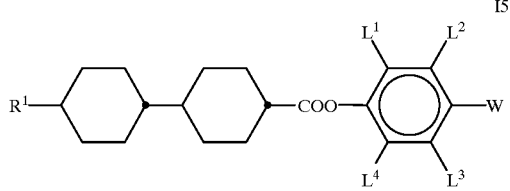

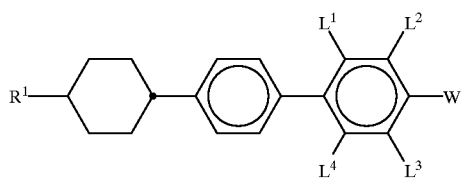

$L^1$, $L^2$, $L^3$ and $L^4$=H. Cl or F.

Preference is given to compounds in which at least one of the radicals $L^1$ and $L^2$ is F. Preference is also given to compounds in which one of the radicals $L^1$ and $L^2$ is F and the other is CF and at the same time $L^3$ and $L^4$ are H. Particular preference is given to compounds in which $L^1$ and $L^2$ are F and at the same time $L^3$ and $L^4$ are H or $L^2$ and $L^3$ are F and at the same time $L^1$ and $L^4$ are H.

Preferred compounds of the subformulae I2 and I6 are those of the formulae I2a, I2b, I2c, I6a and I6b:

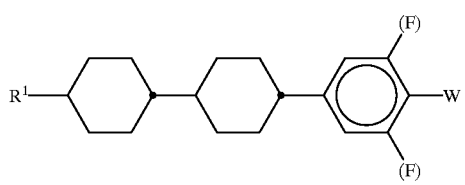

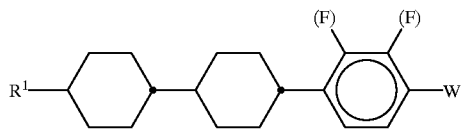

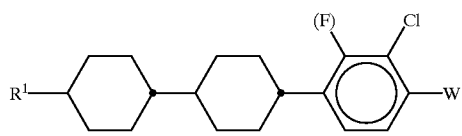
I2c
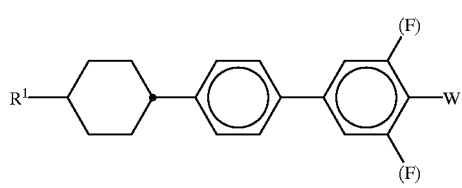
I6a
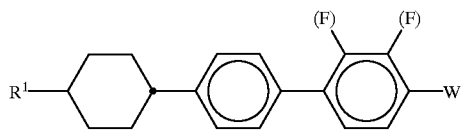
I6b
where (F) is H or F.
Further preferred compounds of the subformulae I2a, I2b and I2c are those of the formulae I2a1, I2b1 to I2b3 and I2c1:
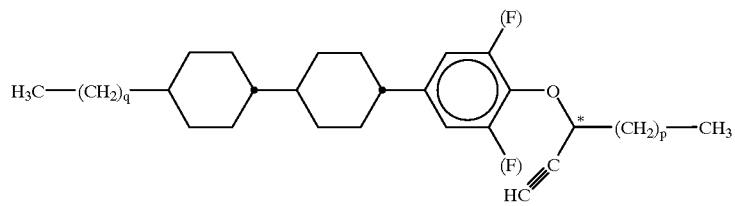
I2a1
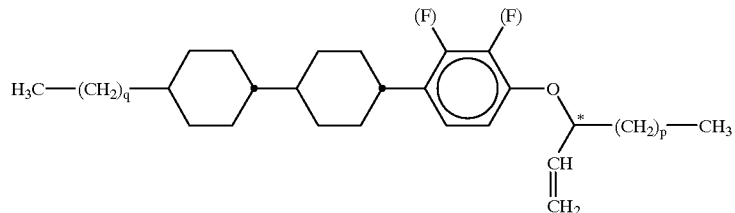
I2b1
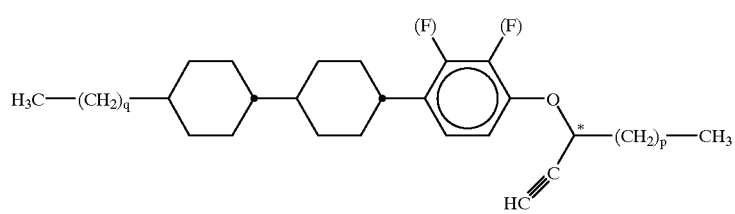
I2b2
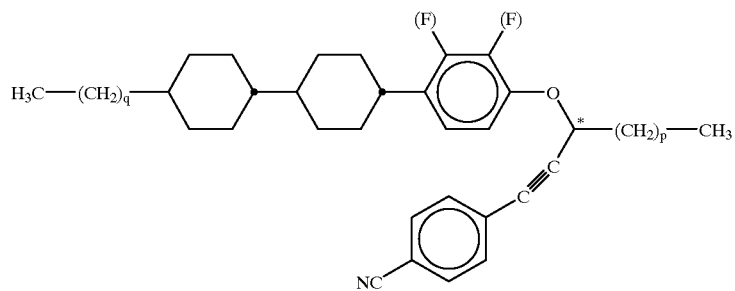
I2b3
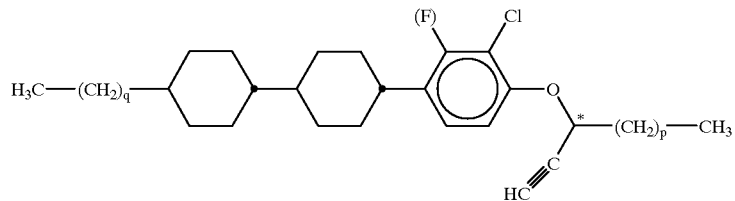
I2c1 p=3, 4, 5, 6, or 7, q=1, 2, 3 or 4, and (F) is H or F.

For AM applications, chiral compounds of the formula I which contain no ester groups are preferred.

The compounds of the formula I are prepared by methods known per se, as described in the literature (for example in the standard works such as Houben-Weyl, Methoden der Organischen Chemie [Methods of Organic Chemistry], Georg-Thieme-Verlag, Stuttgart), under reaction conditions which are known and suitable for such reactions.

Use can also be made here of variants which are known per se, but are not described here in greater detail.

If desired, the starting materials can also be formed in situ by not isolating them from the reaction mixture, but instead immediately converting them into the compounds of the formula I.

The novel compounds can be prepared, for example, in accordance with the following reaction scheme:

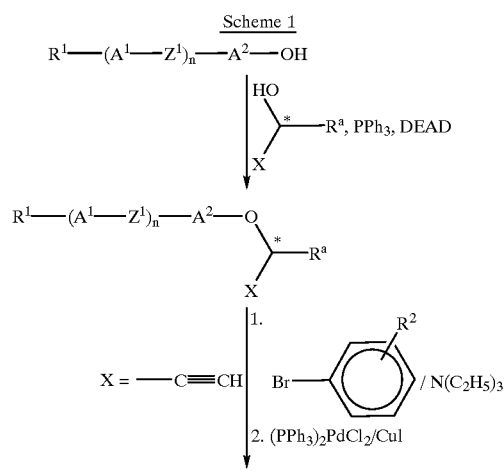

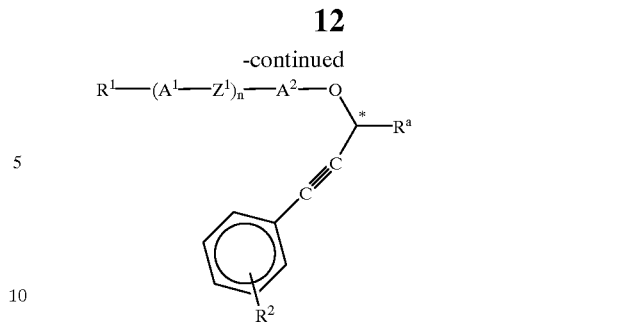

$R^2$ is H, CN, Cl, F or an alkyl, alkenyl or alkoxy radical having 1 to 8 carbon atoms, in which one or more H atoms may be replaced by F atoms. DEAD is diethylazadicarboxylate.

Preferred compounds of the formula I can be prepared analogously to the following scheme

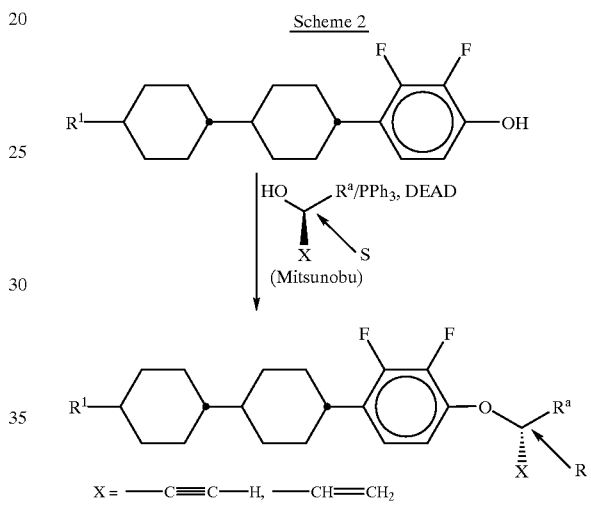

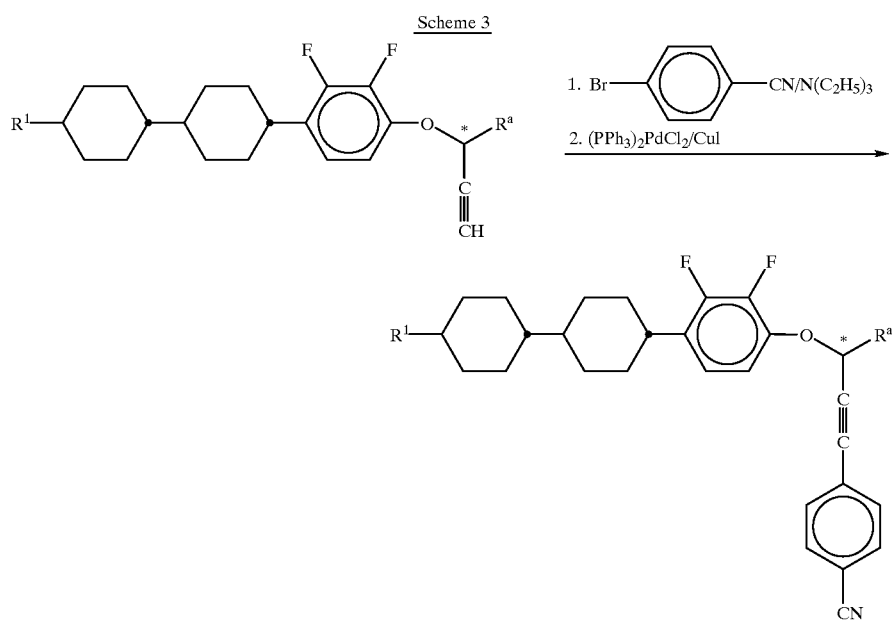

The invention furthermore relates to liquid-crystalline media comprising at least two liquid-crystalline components, characterized in that they include at least one compound of the formula I.

Preference is given to liquid-crystalline media which include one or more compounds of the formula I which contain no ester groups.

In the preferred embodiment of the present invention, the cholesteric pitch of the liquid-crystalline medium which includes at least one compound of the formula I has a temperature dependence such that it results, through its influence on the threshold or addressing voltage, in a low temperature dependence of the threshold or addressing voltage. Temperature dependences of the threshold voltage of less than 0.1%/°C. are preferred. Particular preference is given to temperature dependences of the threshold voltage of 0.05%/°C. and in particular in the range from 0.01 to 0.05%/°C.

A further embodiment of the present invention relates to liquid-crystalline media which include at least one compound of the formula I and have, in the range from T=0° C. to 50° C., a temperature dependence of the cholesteric pitch of, preferably, less than 0.1%/°C., particularly preferably less than 0.05%/°C. In this embodiment, particular preference is given to temperature dependences of less than 0.02%/°C.; temperature dependences of between 0.001 and 0.05%/°C. are also preferred. The abovementioned temperature dependences are absolute amounts. The temperature dependence of the pitch itself can be either positive or negative in accordance with the present invention.

The invention furthermore relates to electro-optical displays containing a liquid-crystalline medium of this type, for example a TN, supertwist or active-matrix liquid-crystal display, having two plane-parallel outer plates which, together with a frame, form a cell, a nematic liquid-crystal mixture of positive dielectric anisotropy located in the cell, electrode layers covered by alignment layers on the insides of the outer plates, a tilt angle between the long axis of the molecules at the surface of the outer plates and the outer plates of from about 1 degree to 30 degrees, and a twist angle of the liquid-crystal mixture in the cell from alignment layer to alignment layer with a value of between 60 and $_{600°}$, preferably from 120° to 360° for STN displays and preferably from 70° to 110° for AM displays, where the nematic liquid-crystal mixture a) is based on component A consisting of one or more compounds having a dielectric anisotropy of from +1.5 to +40, b) comprises 0–40% by weight of a liquid-crystalline component B consisting of one or more compounds having a dielectric anisotropy of between –1.5 and +1.5, c) comprises 0–20% by weight of a liquid-crystaline component C consisting of one or more compounds having a dielectric anisotropy of below –1.5, and d) comprises an optically active component D in an amount such that the ratio between the layer thickness (separation of the plane-parallel outer plates) and the natural pitch of the chiral nematic liquid-crystal mixture is from about 0.2 to 1.3 in STN displays and from about 0.01 to 0.45 in AM displays, the optically active component D includes at least one compound of the formula I, and the nematic liquid-crystal mixture has a nematic phase range of least 60 degrees Celsius, a viscosity at 20° C. of not greater than 35 mPa·s and preferably not greater than 25 mPa·s and in particular not greater than 20 mPa·s, and a dielectric anisotropy of at least +1, where the dielectric anisotropies of the compounds and the parameters of the nematic liquid-crystal mixture are based on a temperature of 20° C., Where the liquid-crystal media are for AM displays, they are based on terminally fluorinated liquid-crystal compounds and where the media are for STN displays, they preferably include, for component A, at least 10% of a cyano-substituted compound. Such media preferably include less than 5% of compounds containing ester groups. For AM displays, the mixtures are particularly preferably based on compounds containing no ester groups. For many such applications, the media consist exclusively of compounds containing no ester groups.

The invention also relates to chiral tilted smectic liquid-crystalline media which include at least one compound of the formula I, in particular a ferroelectric liquid-crystalline medium comprising an achiral smectic component S which includes at least one achiral smectic liquid-crystalline compound, and a chiral component D which includes at least one chiral dopant, where one chiral dopant is a compound of the formula I.

The invention furthermore relates to electro-optical display elements which contain such phases, in particular liquid-crystal switching and display devices containing a ferroelectric liquid-crystalline medium, outer plates, electrodes, at least one alignment layer and, if desired, additional auxiliary layers, where the ferroelectric medium which includes at least one compound of the formula I is a medium having a temperature dependence of the cholesteric pitch in the range from 0° C. to 50° C., of from 0.1% to 10%.

The invention furthermore relates to electro-optical display elements having active-matrix addressing which contain nematic or cholesteric phases which include at least one compound of the formula I.

The term "containing no ester groups" means that the mesogenic group contains no carboxylate groups —O—CO— and/or —CO—O—. Compounds of this type are particularly preferred as base material and as chiral compounds in AM displays.

The novel media include at least one, preferably at least two, compounds of the formula I. The novel ferroelectric media preferably comprise an achiral smectic component S which includes at least one achiral smectic compound, and a chiral component D is at least one chiral dopant, where at least one chiral compound is a compound of the formula I.

Particular preference is given to novel chiral tilted smectic liquid-crystalline phases whose achiral base mixture, besides compounds of the formula I, includes at least one other component of negative or low positive dielectric anisotropy. The chirality is preferably based, in full or part, on chiral compounds of the formula I. These phases preferably include one or two chiral compounds of the formula I. However, it is also possible to employ achiral compounds of the formula I (for example in the form of a racemate), in which case the chirality of the phase is induced by other optically active compounds. If chiral compounds of the formula I are used, mixtures having an enantiomeric excess are suitable besides the pure optical antipodes. The abovementioned further component(s) of the achiral base mixture can make up from 1 to 50%, preferably from 10 to 25%, of the base mixture.

The compounds of the formula I are particularly suitable as components of nematic liquid-crystalline phases, for example for preventing reverse twist.

In particular, the compounds of the formula I can be used as dopants for nematic liquid-crystalline phases for STN and active-matrix displays. The active-matrix displays here are particularly distinguished by a high helical twisting power (HTP) and by high voltage holding ratios. In particular, doped nematic mixtures of this type can easily be purified by treatment with aluminum oxide, with no or virtually no loss of chiral dopant.

A further advantage of using compounds of the formula I in the novel liquid-crystalline media is their good comPatibility with the nematic liquid crystals, which results in very little change, or none at all, in the clearing point of the liquid-crystal mixtures if the compounds of the formula I are used in conventional amounts, which can extend to a few (for example 10 or more) % by weight.

The compounds of the formula I are also distinguished by very good solubility in liquid-crystal media, in particular in those for AMD applications. The compounds of the formula I are thus also particularly suitable for AMD TN displays having high d/P values and improved grey shade display, as described in DE 42 12 744.

If the HTP has a positive temperature dependence, i.e. if the pitch decreases with increasing temperature, in particular at values in the range from 0.1%/°C. to 10%/°C. or more, the compounds of the formula I are also suitable in novel liquid-crystalline media for temperature compensation of the threshold voltage and thus of the operating voltage of TN and STN displays.

The compounds are also particularly suitable for use in guest-host displays having a small cholesteric pitch, for example of the phase-change type.

A further preferred application of the compounds of the formula I is in ferroelectric liquid-crystal mixtures. Here, the compounds are suitable both for inducing spontaneous polarization and for compensating the pitch.

Furthermore, the novel chiral compounds can also be used to prepare liquid-crystalline media for phase-change displays (for example Y. Yabe et al., SID 1991 Digest, 261–264).

These novel liquid-crystalline media consist of 2 to 25, preferably 3 to 15, components, including at least one compound of the formula I. The other constituents are preferably selected from smectic or smectogenic substances, in particular known substances, from the classes consisting of the azoxybenzenes, benzylideneanilines, biphenyls, terphenyls, phenyl or cyclohexyl benzoates, phenyl or cyclohexyl cyclohexanecatboxylates, phenylcyclohexanes, cyclohexylbiphenyls, cyclohexylcyclohexanes, cyclohexylnaphthalenes, 1,4-biscyclohexylbenzenes, 4,4,-biscyclohexylbiphenyls, phenyl- or cyclohexylpyrimidines, phenyl- or cyclohexylpyridazines and N-oxides thereof, phenyl- or cyclohexyldioxanes, phenyl- or cyclohexyl-1,3-dithianes, 1,2-diphenylethanes, 1,2-dicyclo-hexylethanes, 1-phenyl-2-cyclohexylethanes, optionally halogenated stilbenes, benzyl phenyl ethers, tolans and substituted cinnamic acids. The liquid-crystalline mixture is based on the achiral compounds of this type.

The most important compounds which are suitable as constituents of liquid-crystalline phases of this type can be characterized by the formula I', $$R^b\text{-L-G-E-}R^c \quad \text{I'}$$

in which L and E are each a carbocyclic or heterocyclic ring system from the group consisting of 1,4-disubstituted benzene and cyclohexane rings, 4,4'disubstituted biphenyl, phenylcyclohexane and cyclohexylcyclohexane systems, 2,5-disubstituted pyrimidine and 1,3-dioxane rings, 2,6-disubstituted naphthalene, dihydronaphthalene and tetrahydronaphthalene, quinazoline and tetrahydroquinazoline, G is

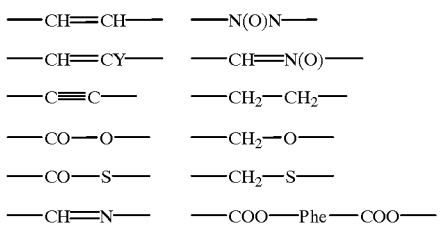

or a C-C single bond;

Y is halogen, preferably chlorine, or —CN, and

—$R^b$ and $R^c$ are alkyl, alkoxy, alkanoyloxy, alkoxycarbonyl or alkoxycarbonyloxy having 1 to 18, preferably 5 to 12, carbon atoms, or one of these radicals is alternatively —F, —$CF_3$, —$OCF_3$ or —CN.

In most of these compounds, $R^b$ and $R^1$ are each alkyl or alkoxy groups of various chain length, where the total number of carbon atoms in nematic media is generally between 2 and 9, preferably between 2 and 5, but in contrast is generally more than 12, preferably 12 to 20, in particular 13 to 18, in ferroelectric media. However, other variants of the proposed substituents are also common. Many such substances or mixtures thereof are commercially available. All these substances are obtainable by methods known from the literature.

The novel media having a nematic phase include from 0.001 to 15% by weight, preferably from 0.1 to 5% by weight, particularly preferably from 0.2 to 2% by weight, of one or more compounds of the formula I. The novel media having a tilted smectic phase include from 0.1 to 40% by weight, preferably from 1 to 30% by weight, of one or more compounds of the formula I. These media furthermore preferably include from 2 to 20% by weight, particularly preferably from 5 to 10% by weight, of one or more compounds of the formula I.

The novel phases are prepared in a manner conventional per se. In general, the components are dissolved in one another, advantageously at elevated temperature.

The mixture components for ferroelectric media are preferably compounds of the following formulae:

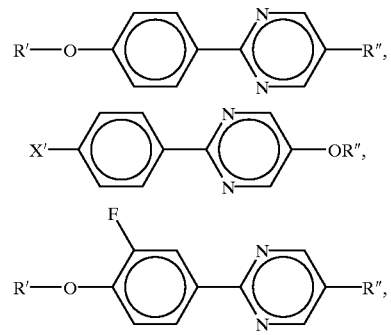

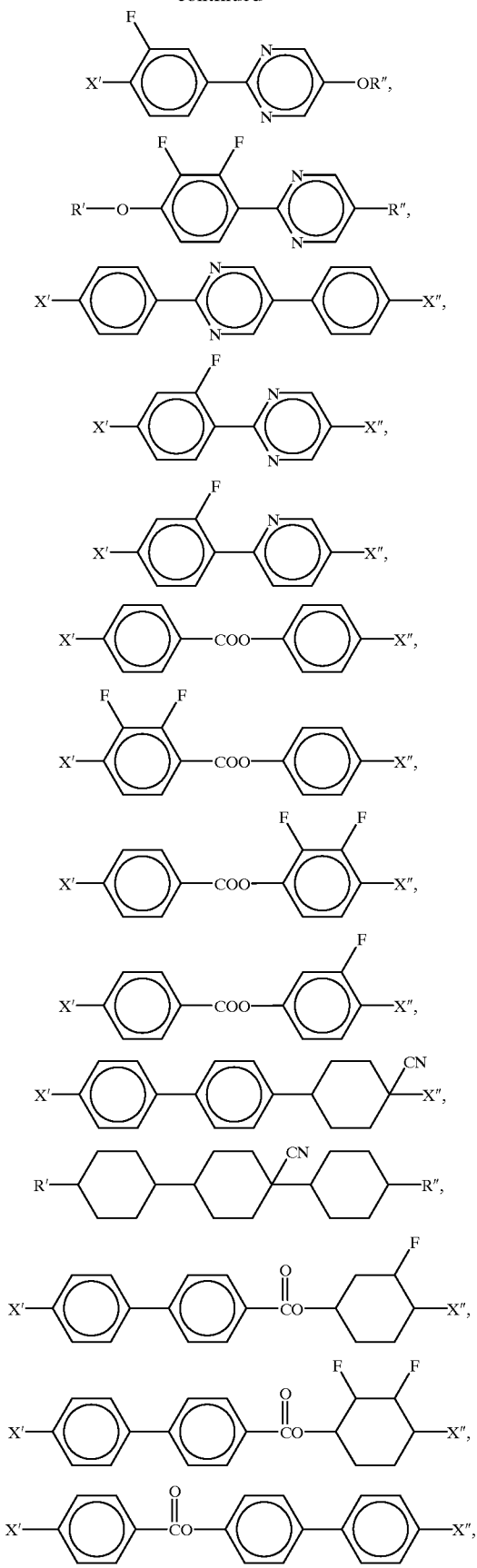
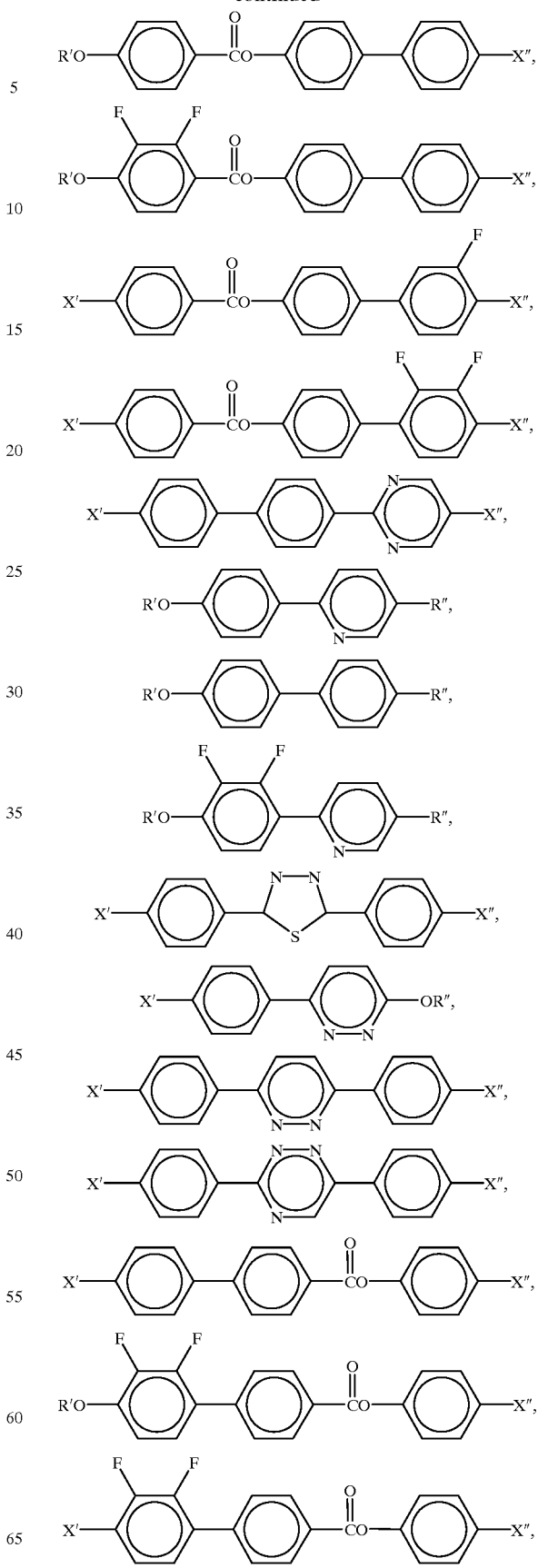

-continued

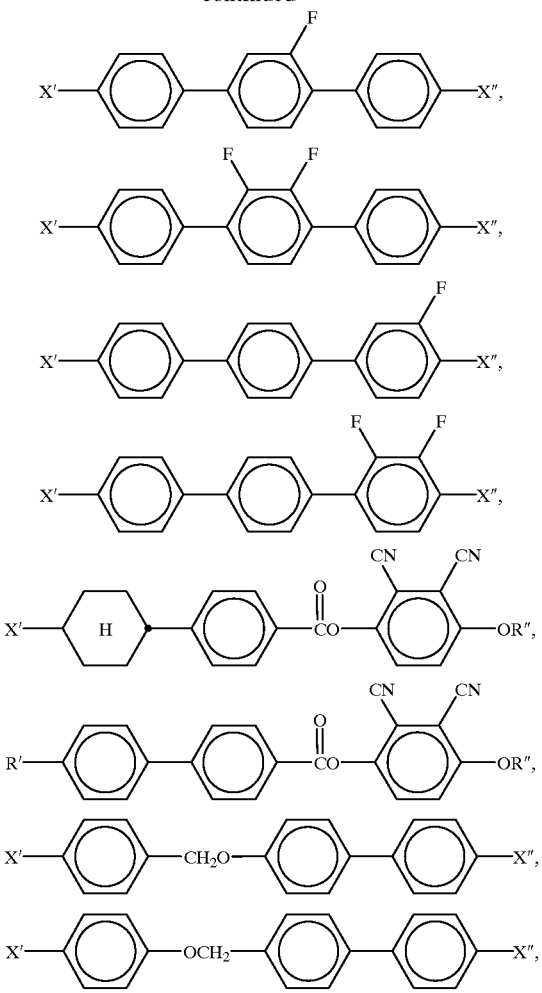

in which R' and R" are each, independently of one another, alkyl having 5 to 18 carbon atoms, and X' and X" are each, independently of one another, alkyl, alkoxy, polyfluoroalkyl or polyfluoroalkoxy having 5 to 18 carbon atoms.

By means of suitable additives, the liquid-crystlline phases of the invention can be modified in a manner such that they can be used in all types of liquid-crystal display elements which have been disclosed hitherto, in particular of the SSFLC type in the chevron or bookshelf geometry.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German application No. 196 44 043.2, filed Oct. 31, 1996 is hereby incorporated by reference.

The examples below are intended to illustrate the invention without representing a limitation. m.p.=melting point, cl.p.=clearing point. Above and below, percentages are percent by weight; all temperatures are given in degrees Celsius. "Conventional work-up" means that water is added, the mixture is extracted with dichloromethane, the phases are separated, the organic phase is dried and evaporated, and the product is purified by crystallization and/or chromatography.

In the present application and in the examples below, the structures of the liquid-crystal compounds are indicated by means of acronyms, with the transformation into chemical formulae taking place in accordance with Tables A and B below. All radicals $C_nH_{2n+1}$ and $C_mH_{2m+1}$ are straight-chain alkyl radicals having n and m carbon atoms respectively. The coding in Table B is self-evident. In Table A, only the acronym for the parent structure is given. The acronym for the parent structure is followed in each individual case, separated by a hyphen, by a code for the substituents $R^1$, $R^2$, $L^1$, $L^2$ and $L^3$:

| Code for $R^1$ $R^2$, $L^1$, $L^2$, $L^3$ | $R^1$ | $R^2$ | $L^1$ | $L^2$ | $L^3$ |
|---|---|---|---|---|---|
| nm | $C_nH_{2n+1}$ | $C_mH_{2m+1}$ | H | H | H |
| nOm | $C_nH_{2n+1}$ | $OC_mH_{2m+1}$ | H | H | H |
| nO.m | $OC_nH_{2n+1}$ | $C_mH_{2m+1}$ | H | H | H |
| n | $C_nH_{2n+1}$ | CN | H | H | H |
| nN.F | $C_nH_{2n+1}$ | CN | H | F | H |
| nF | $C_nH_{2n+1}$ | F | H | H | H |
| nOF | $OC_nH_{2n+1}$ | F | H | H | H |
| nCl | $C_nH_{2n+1}$ | Cl | H | H | H |
| nF.F | $C_nH_{2n+1}$ | F | H | F | H |
| nOmFF | $C_nH_{2n+1}$ | $OC_mH_{2m+1}$ | F | F | H |
| nmF | $C_nH_{2n+1}$ | $C_mH_{2m+1}$ | F | H | H |
| nCF$_3$ | $C_nH_{2n+1}$ | CF$_3$ | H | H | H |
| nOCF$_3$ | $C_nH_{2n+1}$ | OCF$_3$ | H | H | H |
| nOCF$_2$ | $C_nH_{2n+1}$ | OCHF$_2$ | H | H | H |
| nOCF$_2$.F.F | $C_nH_{2n+1}$ | OCHF$_2$ | H | F | F |
| nOCF$_2$.F | $C_nH_{2n+1}$ | OCHF$_2$ | H | F | H |
| nS | $C_nH_{2n+1}$ | NCS | H | H | H |
| rVsN | $C_rH_{2r+1}$—CH=CH—$C_sH_{2s}$— | CN | H | H | H |
| rEsN | $C_rH_{2r+1}$—O—$C_sH_{2s}$— | CN | H | H | H |
| nNF | $C_nH_{2n+1}$ | CN | F | H | H |
| nAm | $C_nH_{2n+1}$ | $COOC_mH_{2m+1}$ | H | H | H |
| nF.F.F | $C_nH_{2n+1}$ | F | H | F | F |
| nOCF$_3$.F | $C_nH_{2n+1}$ | OCF$_3$ | H | F | H |
| nOCF$_3$.F.F | $C_nH_{2n+1}$ | OCF$_3$ | H | F | F |
| nCl.F | $C_nH_{2n+1}$ | Cl | H | F | H |
| nCl.F.F | $C_nH_{2n+1}$ | Cl | H | F | F |

TABLE A

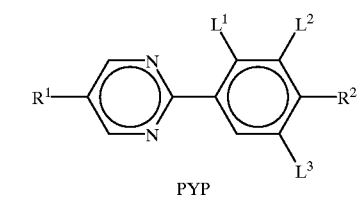

PYP

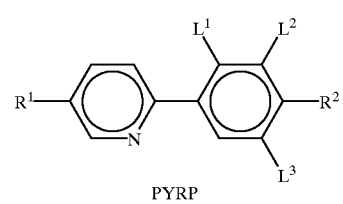

PYRP

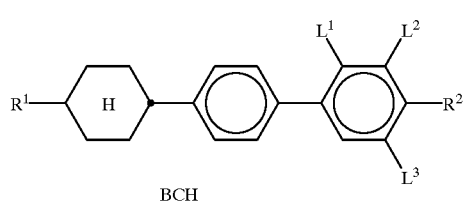

BCH

TABLE A-continued
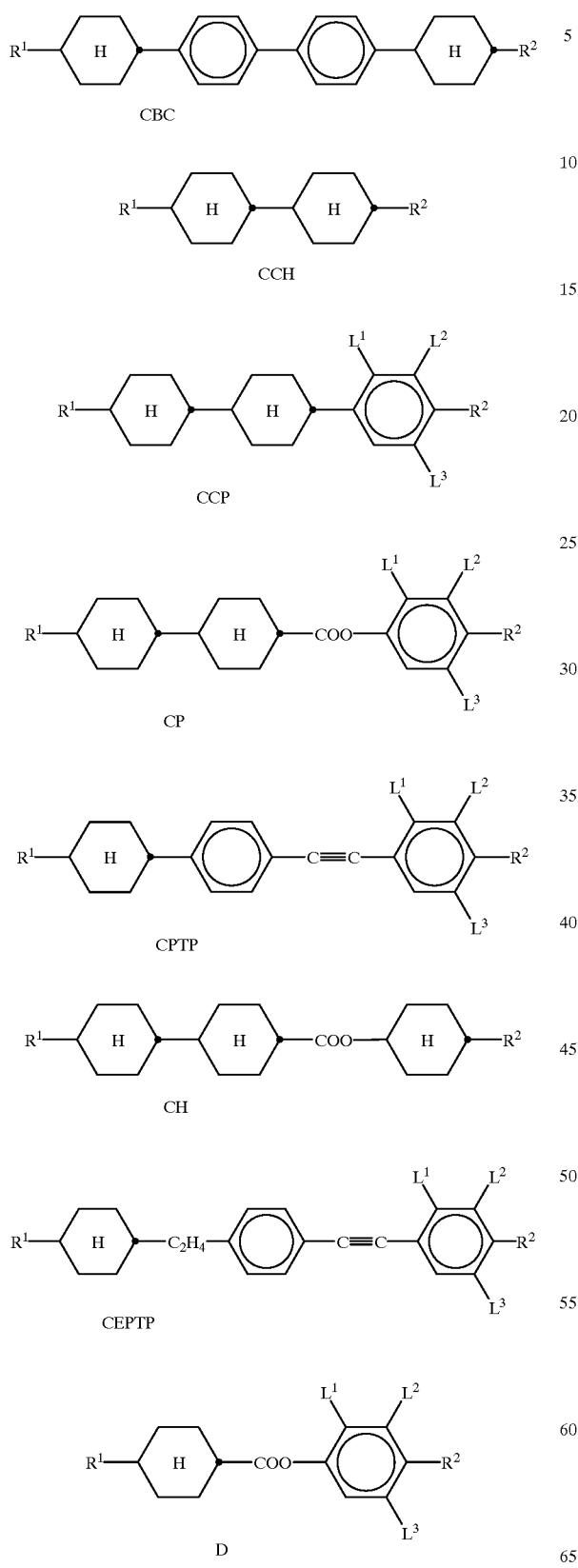
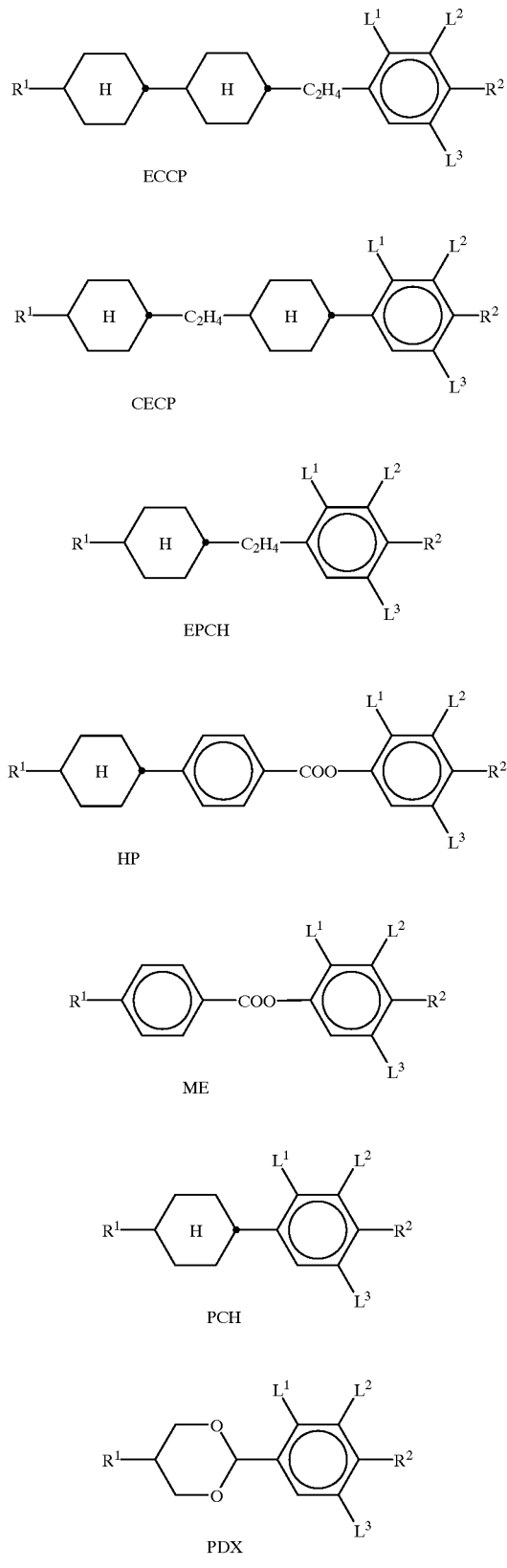

TABLE A-continued
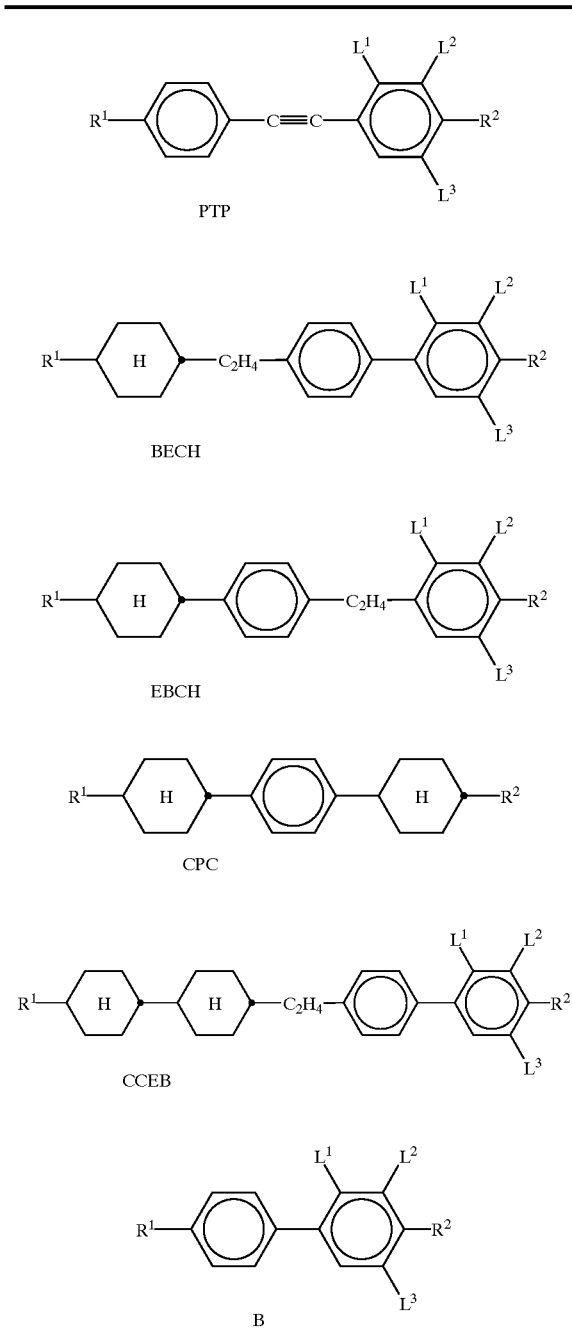
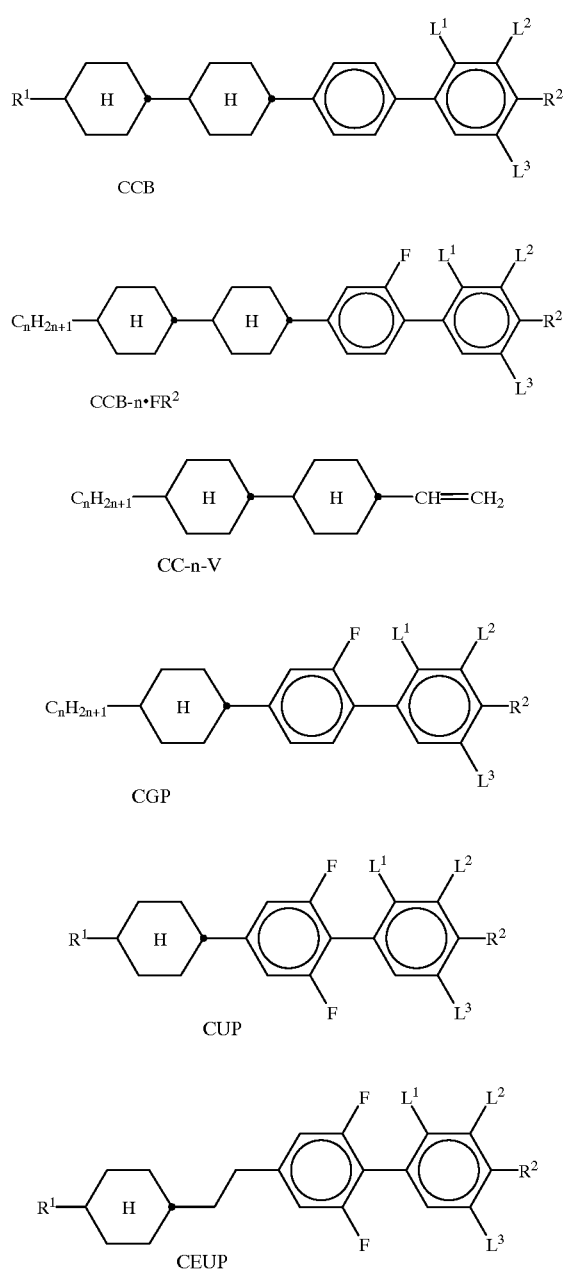

TABLE B
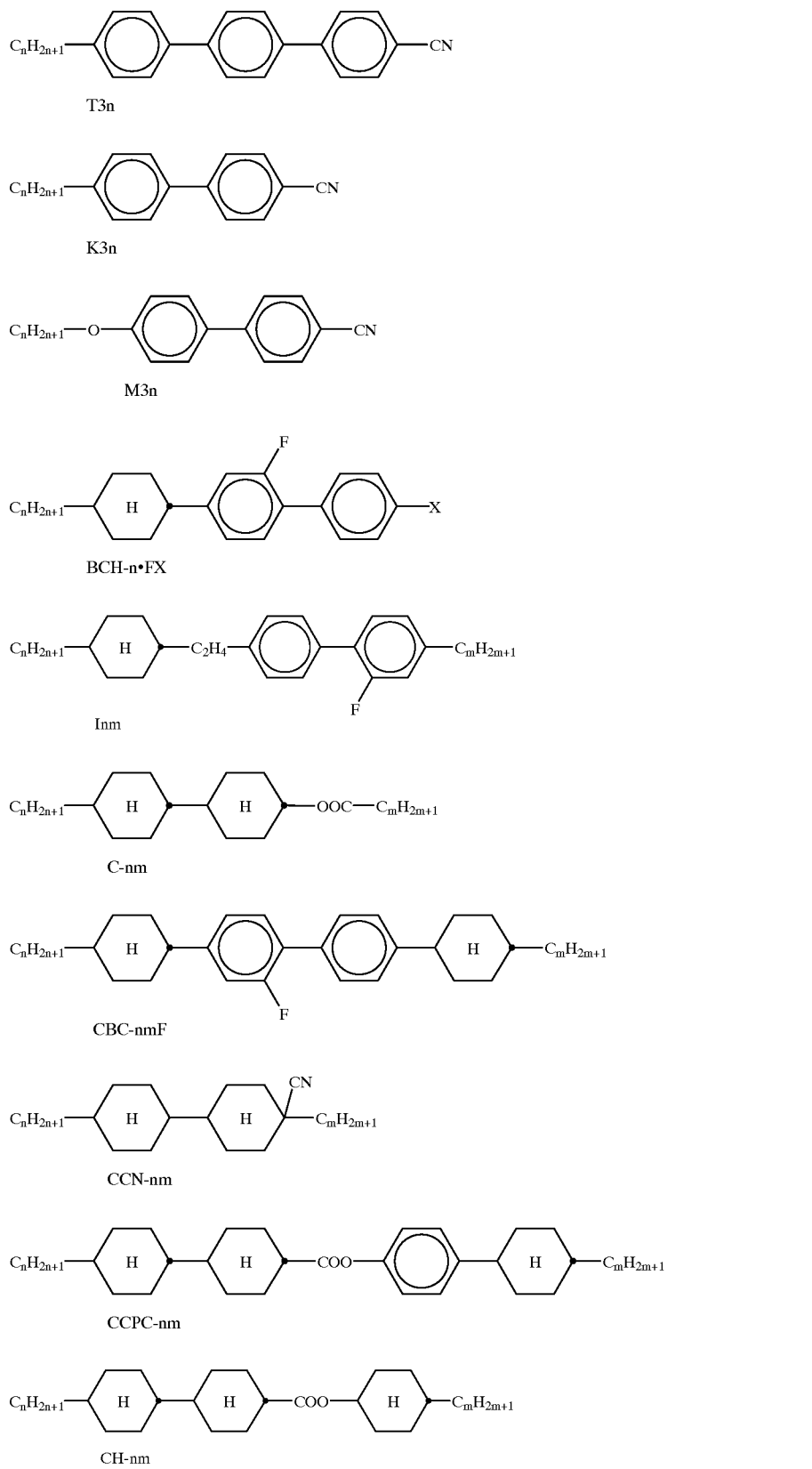

TABLE B-continued
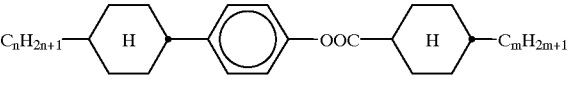
HD-nm
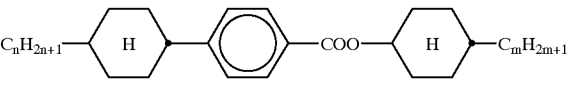
HH-nm
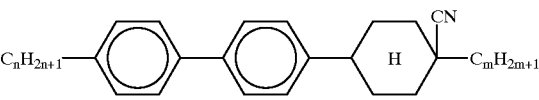
NCB
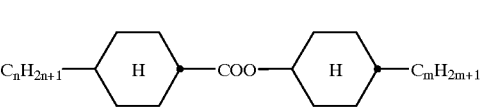
OS-nm
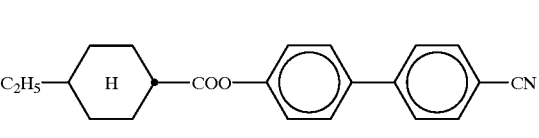
CHE•2
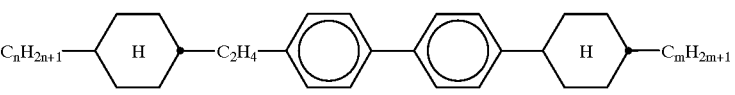
ECBC-nm
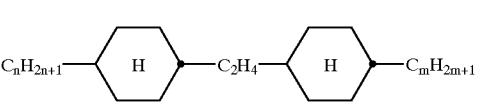
ECCH-nm
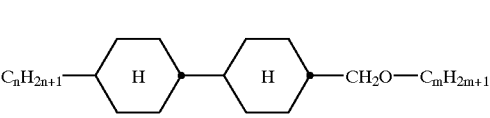
CCH-n1EM
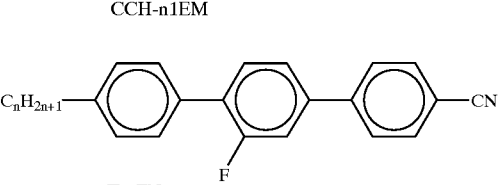
T-nFN
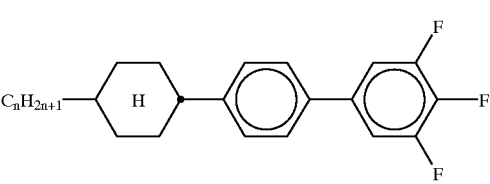
BCH-nF•F•F TABLE B-continued
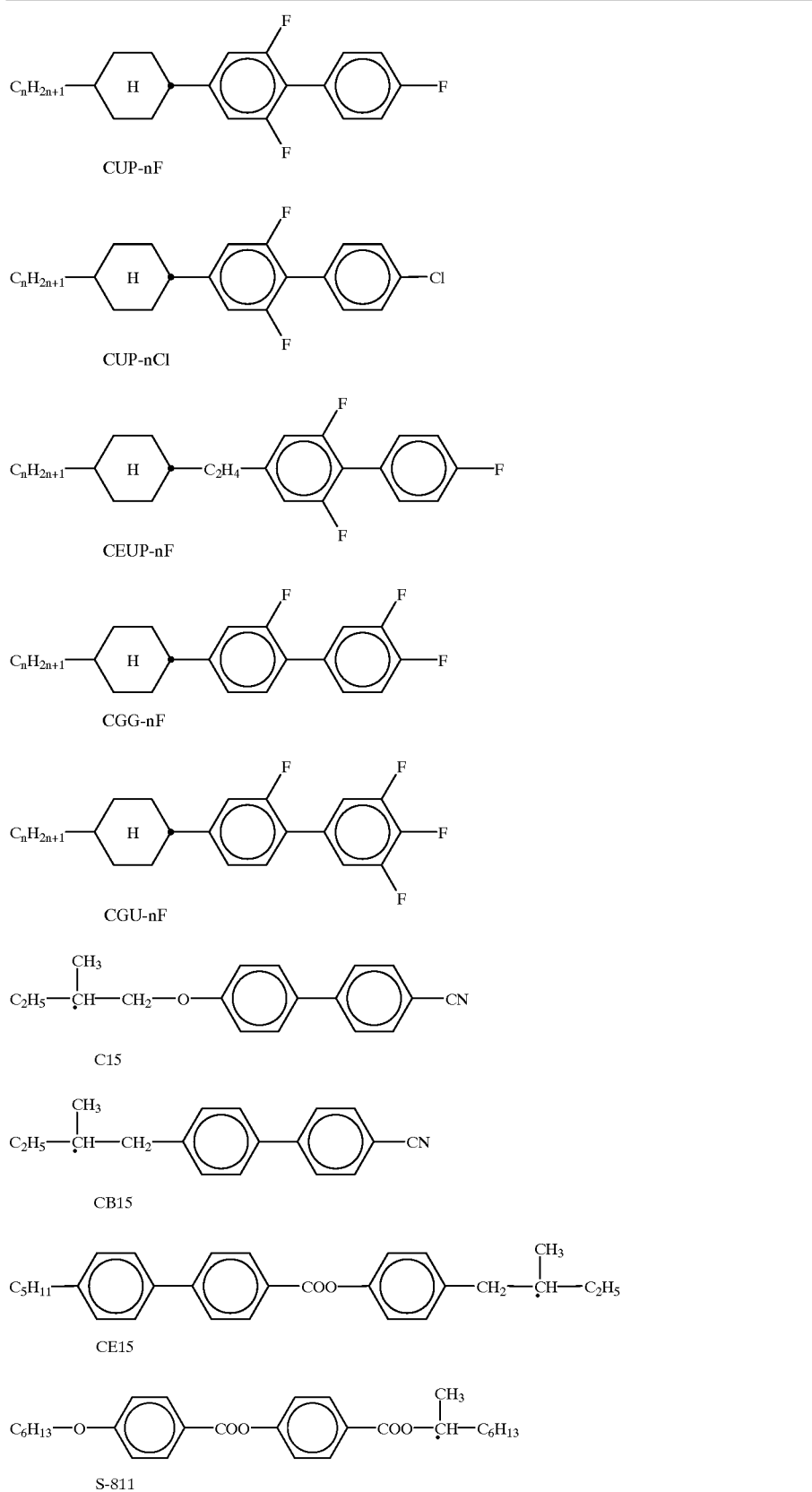

TABLE B-continued

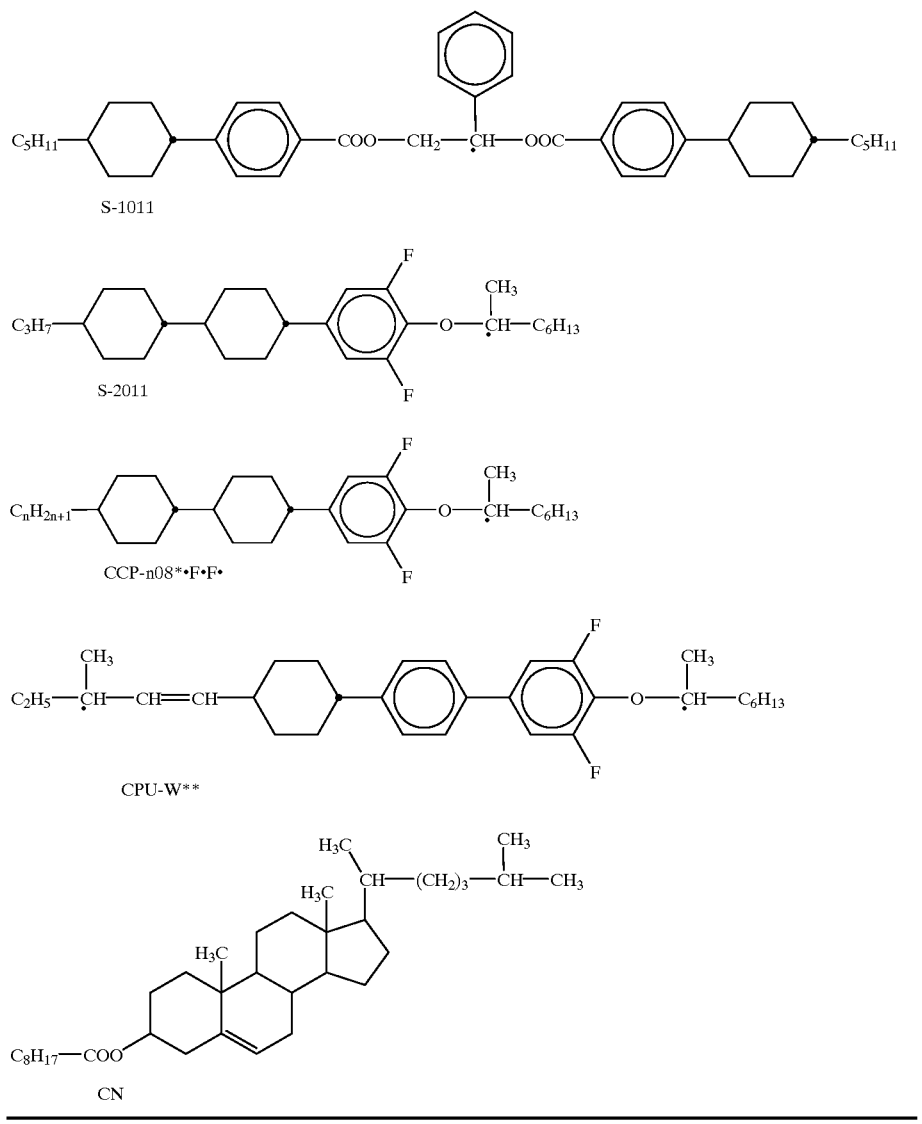

The following abbreviations are also used:
C: Crystalline solid state
S: Smectic phase (the index denotes the phase type, for example $S_C$=smectic C, $S_A$=smectic A)
N: Nematic state
Ch: Cholesteric phase
I: Isotropic phase.
The number between two symbols indicates the conversion temperature in degrees Celsius.
The following abbreviations are used:
$PPh_3$ triphenylphosphine
DEAD diethyl azodicarboxylate
THF tetrahydrofuran
$B(OMe)_3$ trimethyl borate
BuLi butyllithium

EXAMPLES

1

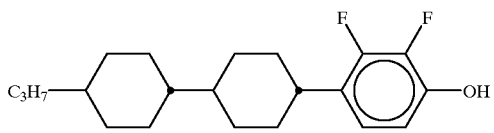

-continued

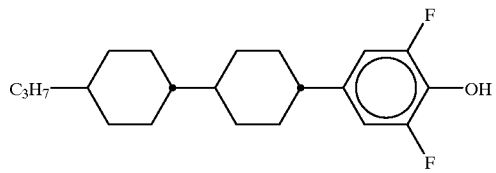
2

Example 1

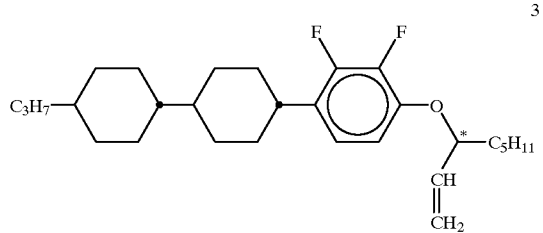
3

10 mmol of diethyl azodicarboxylate are added dropwise at room temperature to a mixture of 9 mmol of 1, 9 mmol of R-(−)-1-octen-3-ol, 9 mmol of triphenylphosphine and 70 ml of THF. The mixture is stirred for 5.5 hours and subjected to conventional work-up. Chromatography gives 3; C 46 I; $[\alpha]^{20}_D = -3.1°$ (CH$_2$Cl$_2$)

Example 2

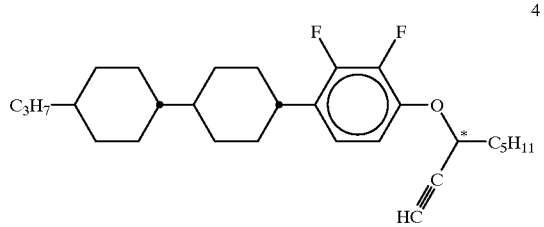
4

140 mmol of diethyl azodicarboxylate (DEAD) are added dropwise at room temperature to a mixture of 119 mmol of 1, 119 mmol of R-(+)-1-octyn-3-ol, 119 mmol of triphenylphosphine and 1000 ml of THF. The mixture is stirred for 12 hours and subjected to conventional work-up. Chromatography gives 4, C 51 S (27.7) N 92.6 I; $[\alpha]^{20}_D = -79.00$ (CH$_2$Cl$_2$).

Example 3

The compound 5 which is enantiomeric to 4 is prepared analogously to Example 2 using (S)-(−)-1-octyn-3-ol and diisopropyl azodicarboxylate instead of DEAD, C 51 S$_B$ (27.3) N 92.2 I; $[\alpha]^{20}_D = 80.1°$ (CH$_2$Cl$_2$)

Example 4

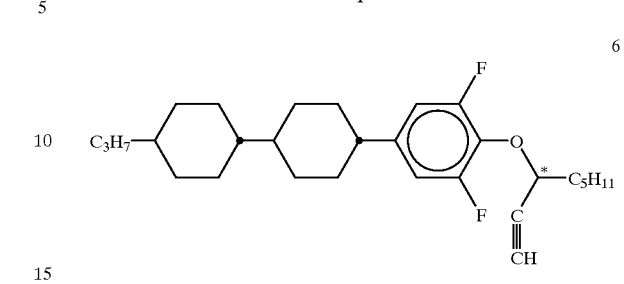
6

Analogously to Example 2, 9 mmol of diethyl azodicarboxylate are added dropwise at room temperature to a mixture of 9 mmol of 2, 8 mmol of R-(+)-1-octyn-3-ol, 8 mmol of triphenylphosphine and 70 ml of THF. The mixture is stirred for 12 hours and subjected to conventional work-up. Chromatography gives 6, C 74 N 89.6 I.

Example 5

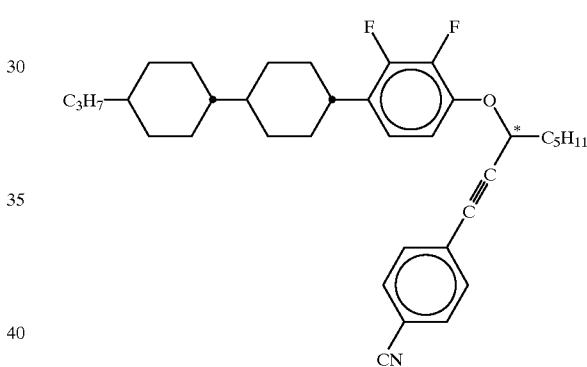
7

0.09 mmol of bis(triphenylphosphine)palladium(II) chloride and 0.045 mmol of copper(I) iodide are added with stirring to a mixture of 4.5 mmol of 5, 4.8 mmol of 4-bromobenzonitrile and 50 ml of triethylamine. The mixture is stirred for a further 60 hours and subjected to conventional work-up. Chromatography gives 7, T$_g$-9 C 82 I; $[\alpha]^{20}_D = 147.10$ (CH$_2$Cl$_2$)

The following (Examples 6–80) were prepared analagously to Examples 1 to 5:

| Compound No. | n | A | B | X | m | |
|---|---|---|---|---|---|---|
| 8 | 2 | cyclohexane | benzene | C≡CH | 5 | |
| 9 | 2 | cyclohexane | benzene | CH=CH$_2$ | 5 | |
| 10 | 2 | cyclohexane | benzene | C≡C—C$_6$H$_4$—CN | 5 | |
| 11 | 3 | cyclohexane | benzene | C≡CH | 5 | C 72 S$_B$ 123 I |
| 12 | 3 | cyclohexane | benzene | CH=CH$_2$ | 5 | S$_B$ 100 I |
| 13 | 3 | cyclohexane | benzene | C≡C—C$_6$H$_4$—CN | 5 | |
| 14 | 5 | cyclohexane | benzene | C≡CH | 5 | |
| 15 | 5 | cyclohexane | benzene | CH=CH$_2$ | 5 | |
| 16 | 5 | cyclohexane | benzene | C≡C—C$_6$H$_4$—CN | 5 | |
| 17 | 3 | benzene | benzene | C≡CH | 5 | |
| 18 | 5 | benzene | benzene | C≡CH | 5 | |
| 19 | 3 | cyclohexane | benzene | C≡CH | 6 | |

-continued
| Compound No. | n | A | B | X | m |
|---|---|---|---|---|---|
| 20 | 3 | 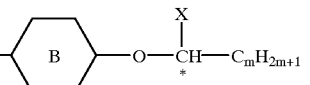 |  | C≡CH | 7 |
| 21 | 2 |  |  | C≡CH | 5 |
| 22 | 2 | 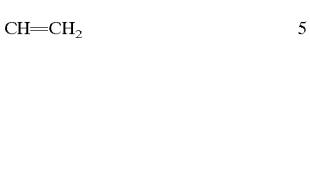 | 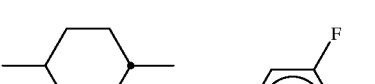 | CH=CH₂ | 5 |
| 23 | 2 | 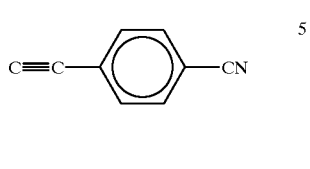 |  | 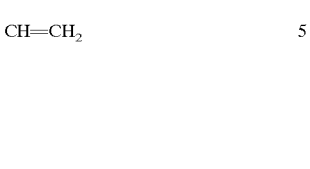 | 5 |
| 24 | 3 |  | 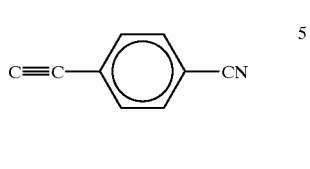 | CH=CH₂ | 5 |
| 25 | 3 |  |  | | 5 |
| 26 | 5 | | | C≡CH | 5 |

-continued $$C_nH_{2n+1}-\bigcirc-A-B-O-\overset{X}{\underset{*}{CH}}-C_mH_{2m+1}$$

| Compound No. | n | A | B | X | m |
|---|---|---|---|---|---|
| 27 | 3 | phenyl | 2,3,5-trifluorophenyl (F top, F bottom) | C≡CH | 5 |
| 28 | 5 | phenyl | 2,3,5-trifluorophenyl | C≡CH | 5 |
| 29 | 5 | cyclohexyl | 2,3,5-trifluorophenyl | C≡CH | 6 |
| 30 | 5 | cyclohexyl | 2,3,5-trifluorophenyl | C≡CH | 7 |
| 31 | 2 | cyclohexyl | 2,3-difluorophenyl | C≡CH | 5 C 51 N 54.7 I |
| 32 | 2 | cyclohexyl | 2,3-difluorophenyl | CH=CH$_2$ | 5 |
| 33 | 2 | cyclohexyl | 2,3-difluorophenyl | C≡C—C$_6$H$_4$—CN | 5 |
| 34 | 5 | cyclohexyl | 2,3-difluorophenyl | C≡CH | 5 C 47 S$_B$ 86 N 100.2 I |

-continued

| Compound No. | n | A | B | X | m |
|---|---|---|---|---|---|
| 35 | 5 | cyclohexyl | 2,3-difluorophenyl | CH=CH₂ | 5 |
| 36 | 5 | cyclohexyl | 2,3-difluorophenyl | C≡C—C₆H₄—CN | 5 |
| 37 | 3 | phenyl | 2,3-difluorophenyl | C≡CH | 5 |
| 38 | 3 | phenyl | 2,3-difluorophenyl | CH=CH₂ | 5 |
| 39 | 3 | phenyl | 2,3-difluorophenyl | C≡C—C₆H₄—CN | 5 |
| 40 | 5 | phenyl | 2,3-difluorophenyl | C≡CH | 5 |
| 41 | 5 | phenyl | 2,3-difluorophenyl | CH=CH₂ | 5 |
| 42 | 5 | phenyl | 2,3-difluorophenyl | C≡C—C₆H₄—CN | 5 |
| 43 | 3 | cyclohexyl | 2,3-difluorophenyl | C≡CH | 6 |

-continued

| Compound No. | n | A | B | X | m |
|---|---|---|---|---|---|
| 44 | 3 | cyclohexyl | 2,3-difluorophenyl | CH=CH$_2$ | 6 |
| 45 | 3 | cyclohexyl | 2,3-difluorophenyl | C≡C—C$_6$H$_4$—CN | 6 |
| 46 | 3 | cyclohexyl | 2,3-difluorophenyl | C≡CH | 7 |
| 47 | 3 | cyclohexyl | 2,3-difluorophenyl | CH=CH$_2$ | 7 |
| 48 | 3 | cyclohexyl | 2,3-difluorophenyl | C≡C—C$_6$H$_4$—CN | 7 |
| 49 | 3 | cyclohexyl | 3-fluorophenyl | C≡CH | 5  C 42 N 87.0 I |
| 50 | 3 | cyclohexyl | 3-fluorophenyl | CH=CH$_2$ | 5 |
| 51 | 3 | cyclohexyl | 3-fluorophenyl | C≡C—C$_6$H$_4$—CN | 5 |
| 52 | 5 | cyclohexyl | 3-fluorophenyl | C≡CH | 5 |

-continued $C_nH_{2n+1}$—[cyclohexane]—[A]—[B]—O—CH(X)*—$C_mH_{2m+1}$

| Compound No. | n | A | B | X | m |
|---|---|---|---|---|---|
| 53 | 5 | [cyclohexane] | [benzene-F] | CH=CH$_2$ | 5 |
| 54 | 5 | [cyclohexane] | [benzene-F] | C≡C—[benzene]—CN | 5 |
| 55 | 3 | [cyclohexane] | [benzene-F] | C≡CH | 6 |
| 56 | 3 | [cyclohexane] | [benzene-F] | C≡CH | 7 |
| 57 | 3 | [cyclohexane] | [benzene-F] | C≡CH | 5 |
| 58 | 3 | [cyclohexane] | [benzene-F] | CH=CH$_2$ | 5 |
| 59 | 3 | [cyclohexane] | [benzene-F] | C≡C—[benzene]—CN | 5 |
| 60 | 5 | [cyclohexane] | [benzene-F] | C≡CH | 5 |
| 61 | 5 | [cyclohexane] | [benzene-F] | CH=CH$_2$ | 5 |

-continued $C_nH_{2n+1}$—[cyclohexane]—A—B—O—CH(X)—$C_mH_{2m+1}$
(* on CH)

| Compound No. | n | A | B | X | m | |
|---|---|---|---|---|---|---|
| 62 | 5 | cyclohexane | phenyl-F | C≡C—C6H4—CN | 5 | |
| 63 | 3 | cyclohexane | phenyl-F | C≡CH | 6 | |
| 64 | 3 | cyclohexane | phenyl-F | C≡CH | 7 | |
| 65 | 3 | cyclohexane | phenyl-F,Cl | C≡CH | 5 | C 58 $S_B$ (23) $S_A$ (33) N 81.2 I |
| 66 | 3 | cyclohexane | phenyl-F,Cl | CH=CH₂ | 5 | |
| 67 | 3 | cyclohexane | phenyl-F,Cl | C≡C—C6H4—CN | 5 | |
| 68 | 5 | cyclohexane | phenyl-F,Cl | C≡CH | 5 | |
| 69 | 5 | cyclohexane | phenyl-F,Cl | CH=CH₂ | 5 | |
| 70 | 5 | cyclohexane | phenyl-F,Cl | C≡C—C6H4—CN | 5 | |

-continued $$C_nH_{2n+1}-\text{cyclohexyl}-A-B-O-\overset{X}{\underset{*}{C}H}-C_mH_{2m+1}$$

| Compound No. | n | A | B | X | m |
|---|---|---|---|---|---|
| 71 | 3 | cyclohexyl | phenyl (3-F, 4-Cl) | C≡CH | 6 |
| 72 | 3 | cyclohexyl | phenyl (3-F, 4-Cl) | CH=CH$_2$ | 6 |
| 73 | 3 | cyclohexyl | phenyl (3-F, 4-Cl) | C≡C—C$_6$H$_4$—CN | 6 |
| 74 | 3 | cyclohexyl | phenyl (3-Cl, 4-F) | C≡CH | 5 |
| 75 | 3 | cyclohexyl | phenyl (3-Cl) | C≡CH | 5 |
| 76 | 3 | cyclohexyl | phenyl (2-Cl) | C≡CH | 5 |
| 77 | 3 | cyclohexyl | phenyl (2-Cl, 3-Cl) | C≡CH | 5 |
| 78 | 3 | cyclohexyl | phenyl | C≡C—C$_6$H$_4$—CH$_3$ | 5 |
| 79 | 3 | cyclohexyl | phenyl | C≡C—C$_6$H$_4$(3-CH$_3$) | 5 |

-continued

[Structure: $C_nH_{2n+1}$—cyclohexyl—A—B—O—CH(X)—$C_mH_{2m+1}$, with * indicating chiral center]

| Compound No. | n | A | B | X | m |
|---|---|---|---|---|---|
| 80 | 3 | cyclohexyl | phenyl | C≡C—(2-CH₃-phenyl) | 5 |
| 81 | 3 | cyclohexyl | phenyl | C≡C—(4-C₃H₇-phenyl) | 5 |
| 82 | 3 | cyclohexyl | phenyl | C≡C—(4-C₄H₉-phenyl) | 5 |

The substances in which X is CH=CH₂ which are shown in the table above were synthesized analogously to Example 1. The compounds in which X is C≡CH which are shown in this table were prepared analogously to Example 2. Compounds in this table in which X is

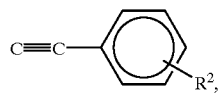

where $R^2$ is CN, CH₃, C₃H₇ or C₄H₉, were synthesized analogously to Example 5.

Examples (use)
Compositions of the mixtures used
Composition of mixture A

| Substance | % by weight |
|---|---|
| ME2N.F | 2.0 |
| ME3N.F | 2.0 |
| ME5N.F | 4.0 |
| PYP-5F | 10.0 |
| CCH-301 | 10.0 |
| CCH-303 | 9.0 |
| PCH-301 | 16.0 |
| CH-33 | 4.0 |
| CH-35 | 4.0 |
| CH-43 | 4.0 |
| CH-45 | 4.0 |
| CP-33F | 8.0 |
| CP-35F | 8.0 |
| CCPC-33 | 5.0 |
| CCPC-34 | 5.0 |
| CCPC-35 | 5.0 |

Properties of mixture A
T(S—N)<−40° C.
Clearing point T (N,I) =103° C.
Viscosity (20° C.)=20 mm² s⁻¹

Dielectric anisotropy (1 kHz, 20° C.)=4.0
Optical anisotropy (20° C.; 589 nm)=0.088
Composition of mixture B

| Substance | % by weight |
|---|---|
| PCH-5F | 10.0 |
| PCH-6F | 8.0 |
| PCH-7F | 6.0 |
| CCP-20CF₃ | 8.0 |
| CCP-30CF₃ | 12.0 |
| CCP-40CF₃ | 7.0 |
| CCP-50CF₃ | 11.0 |
| BCH-3F.F | 12.0 |
| BCH-5F.F | 10.0 |
| ECCP-30CF₃ | 5.0 |
| ECCP-50CF₃ | 5.0 |
| CBC-33F | 2.0 |
| CBC-53F | 2.0 |
| CBC-55F | 2.0 |

Properties of mixture B
T(S—N)<−40° C.
Clearing point T (N,I)=92° C.
Optical anisotropy (20° C.; 589 nm)=0.097
Composition of mixture C

| Substance | % by weight |
|---|---|
| PCH-3 | 18.0 |
| PCH-4 | 12.0 |
| PCH-5 | 21.0 |
| PCH-301 | 6.0 |
| CCH-303 | 14.0 |
| CBC-33 | 5.0 |
| CBC-53 | 5.0 |
| CBC-55 | 4.0 |
| CBC-33F | 5.0 |

-continued

| Substance | % by weight |
|---|---|
| CBC-53F | 5.0 |
| CBC-55F | 5.0 |

Properties of mixture C
T(S—N)<-40° C.
Clearing point T (N,I) =100C
Optical anisotropy (20° C; 589 nm) 0.123
Composition of mixture D

| Substance | % by weight |
|---|---|
| PCH-7F | 8.5 |
| CCP-20CF$_3$ | 7.2 |
| CCP-30CF$_3$ | 6.1 |
| CCP-40CF$_3$ | 5.7 |
| CCP-50CF$_3$ | 5.7 |
| ECCP-3F.F | 5.2 |
| ECCP-5F.F | 5.2 |
| ECCP-3F | 2.5 |
| CUP-3F.F | 3.2 |
| CUP-5F.F | 3.0 |
| CCP-20CF$_2$.F.F | 4.6 |
| CCP-30CF$_2$.F.F | 10.4 |
| CCP-50CF$_2$.F.F | 9.2 |
| CBC-33F | 3.6 |
| BCH-2F.F | 2.1 |
| BCH-3F.F | 2.7 |
| BCH-5F.F | 2.8 |
| BCH-32F | 1.8 |
| BCH-52F | 1.7 |
| PCH-301 | 5.0 |
| CCH-303 | 2.0 |
| CBC-53F | 1.8 |

Properties of mixture D
T(S—N)<-40° C.
Clearing point T (N,I) 98° C.
Optical anisotropy (20° C.; 589 nm)=0.095
Composition of mixture E

| Substance | % by weight |
|---|---|
| ME2N.F | 3.0 |
| ME3N.F | 2.0 |
| ME4N.F | 5.0 |
| ME5N.F | 4.0 |
| PYP-5F | 10.0 |
| CCH-301 | 11.0 |
| CCH-303 | 8.0 |
| CCH-34 | 9.0 |
| PCH-301 | 7.0 |
| CH-33 | 2.0 |
| CH-35 | 2.0 |
| CH-43 | 2.0 |
| CP-33F | 8.0 |
| CP-35F | 8.0 |
| CCPC-33 | 5.0 |
| CCPC-34 | 5.0 |
| CCPC-35 | 5.0 |
| CBC-33 | 2.0 |
| CBC-53 | 2.0 |

Properties of mixture E
T(S—N)<-40° C.
Clearing point T (N,I)=102° C.
Optical anisotropy (20° C.; 589 nm)=0.096
The compositions of mixtures F, G, H and I are given in Use Example AB 6.

Composition of mixture J

| Substance | % by weight |
|---|---|
| ME2N.F | 2.0 |
| ME3N.F | 2.0 |
| ME4N.F | 4.0 |
| PYP-5F | 8.0 |
| CCH-301 | 10.0 |
| CCH-303 | 6.0 |
| CCH-501 | 4.0 |
| PCH-301 | 3.0 |
| BCH-3F.F | 9.0 |
| CC-5-V | 13.0 |
| CP-33F | 5.0 |
| CP-35F | 5.0 |
| CP-55F | 5.0 |
| CH-33 | 4.0 |
| CBC-33 | 4.0 |
| CBC-53 | 2.0 |
| CBC-55 | 3.0 |
| CBC-33F | 3.0 |
| CCPC-33 | 2.0 |
| CCPC-34 | 4.0 |

CCPC-35 2.0
Properties of mixture J:
T(S—N)<-40° C.
Clearing point T (N,I)=109.0° C.
Optical anisotropy (20° C.; 589 nm)=0.100
The compositions of mixtures K and L are shown in Use Example AB 5.
The composition of Mixture M is shown in Use Example AB 7.
Composition of mixture N:

| Substance | % by weight |
|---|---|
| ME2N.F | 4.0 |
| ME3N.F | 4.0 |
| ME4N.F | 13.8 |
| ME5N.F | 13.4 |
| PCH-3 | 10.2 |
| PCH-301 | 7.0 |
| CCH-301 | 6.4 |
| PTP-201 | 2.4 |
| ECCP-3F.F | 2.0 |
| ECCP-5F.F | 2.0 |
| CP-33F | 6.2 |
| CP-35F | 6.2 |
| CP-55F | 3.2 |
| CCPC-33 | 1.2 |
| CCPC-34 | 1.2 |
| CCPC-35 | 1.2 |
| CBC-33F | 2.4 |
| CBC-53F | 2.4 |
| CBC-55F | 2.4 |
| CBC-33 | 1.8 |
| CBC-53 | 1.8 |
| CPTP-30CF$_3$ | 2.4 |
| CPTP-50CF$_3$ | 2.4 |

Properties of mixture N:
Clearing point T (N,I)=89° C.
Optical anisotropy (20° C.; 589 nm)=0.137
The compositions of mixtures O, P, Q, R and S are shown in use example AB 8.
Use Example AB 1
The novel compounds 3 to 7, 11, 12, 31, 34, 49 and 57 are dissolved in liquid-crystal mixture A in the % by weight given in each case in Table I.
The helical pitch (according to Grand-Jean Cano, as described in Hochgesand et al. "HTP of Chiral Dopants in Nematic LCs", Merck, October 1989) of the resultant doped mixtures is measured, and the HTP is calculated therefrom:

$$HPT=[c \cdot p]^{-1}$$

The values thus obtained are shown in Table I below:
Table I
Helical twisting power (HTP) of novel compounds in mixture A as a function of temperature

| No. | Substance | Concentration/% | HTP (T)/$\mu m^{-1}$ T = 0° C. | T = 20° C. | T = 50° C. | HTP (0° C.)/ HTP (50° C.) |
|---|---|---|---|---|---|---|
| AB 1-1 | 3 | 3 | −2.65 | −3.13 | −3.60 | 0.74 |
| AB 1-2 | 4 | 3 | −0.48 | −0.94 | −1.60 | 0.30 |
| AB 1-3 | 5 | 8 | +0.40 | +1.09 | +1.72 | 0.23 |
| AB 1-4 | 6 | 1 | −7.05 | −6.96 | −6.82 | 1.03 |
| AB 1-5 | 7 | 5 | +2.47 | +3.11 | +3.34 | 0.74 |
| AB 1-6 | 11 | 5 | +3.63 | +2.98 | +2.30 | 1.56 |
| AB 1-7 | 12 | 5 | — | −0.58 | −1.40 | — |
| AB 1-8 | 31 | 10 | −0.45 | −1.09 | −1.81 | 0.25 |
| AB 1-9 | 34 | 5 | −0.79 | −1.01 | −1.64 | 0.48 |
| AB 1-10 | 49 | 5 | −3.62 | −3.02 | −2.26 | 1.60 |
| AB 1-11 | 57 | 5 | +0.40 | +0.62 | +1.34 | 0.30 | for AB1-1: HTP (10° C.)=−2.94 $\mu m^{-1}$; HTP (30° C.)=−3.30 $\mu m^{-1}$; HTP (40° C.)=−3.42 $\mu m^{-1}$ for AB1-2: HTP (10° C.)=−0.63 $\mu m^{-1}$; HTP (30° C.)=−1.12 $\mu m^{-1}$; HTP (40° C.)=−1.36 $\mu m^{-1}$ Comparative Example VB 1
In the same way as in Use Example AB 1 , the HTP of the five known compounds CB 15, CN, CPU-W, S-811 and S-1011 in mixture A was determined. The compounds CB 15,CN, S-811 and S-1011 are commercial products from Merck KGaA, Damrstadt. CPU-W is described in DE 19542849.8— The measurement results are shown in Table II.

Table II
HTP of known compounds in mixture A as a function of temperature (comParative examples)

| No. | Substance | Concentration/% | HTP (T)/$\mu m^{-1}$ T = 0° C. | T = 10° C. | T = 20° C. | T = 30° C. | T = 40° C. | T = 50° C. | HTP (0° C.)/ HPT (50° C.) |
|---|---|---|---|---|---|---|---|---|---|
| VB 1-1 | CB 15 | 1 | +6.9 | +6.8 | +6.6 | +6.5 | +6.4 | +6.2 | 1.11 |
| VB 1-2 | CN | 1 | −5.9 | −5.83 | −5.77 | −5.70 | −5.64 | −5.57 | 1.06 |
| VB 1-3 | CPU-W** | 1 | +8.64 | n.m. | +8.64 | n.m. | n.m. | +8.50 | 1.02 |
| VB 1-4 | S-811 | 1 | −10.0 | −10.0 | −9.9 | −9.9 | −9.9 | −9.8 | 1.02 |
| VB 1-5 | S-1011 | 0.3 | −25.4 | −25.8 | −26.7 | −27.9 | −27.8 | −28.3 | 0.90 | n.m not measured

As can be seen from Tables I and II, the novel compounds 4, 5, 31 and 57 have the greatest temperature dependence. Compounds 3, 7, 11, 34 and 49 also have a greater temperature dependence than S-1011 or CB 15, the chiral substances with the greatest temperature dependences of the comParative substances investigated here. Compound 6 has a very low temperature dependence of the HTP, comParable with CN, CPU-W** and S-811.

Use Example AB 2

The novel compound 4 was dissolved to the extent of 8% in liquid-crystal mixture B, and its HTP was measured in a wedge cell for pitch determination (AB 2-1). The mixture was subsequently irradiated with UV light for 100 hours in a SUNTEST instrument from Heraeus (radiation intensity: 35 mW/cm$^2$), and the HTP was re-measured as a function of temperature (AB 2—2). The results determined before and after UV exposure are shown in Table III.

TABLE III

| | | HTP of compound 4 in mixture B | | | |
|---|---|---|---|---|---|
| No. | UV exposure/ h | HTP (T)/$\mu m^{-1}$ T = 0° C. | T = 20° C. | T = 50° C. | HTP (0° C.)/ HTP (50° C.) |
| AB 2-1 | 0 | −3.29 | −3.44 | −3.61 | 0.91 |
| AB 2-2 | 100 | −3.27 | −3.38 | −3.59 | 0.91 |

Table III shows that the HTP and thus also the pitch are not changed significantly by UV irradiation.

Use Example AB 3

Furthermore, the photochemical and thermal stability of compound 4 was determined by measuring the clearing point. To this end, a 10% solution of the substance to be tested in mixture B was investigated. In order to measure the photochemical stability, the clearing point of the mixture was determined before filling of the cells thermostated at 20° C. and re-measured after completion of the UV exposure (AB 3-1). It dropped only slightly from an initial value before exposure of 91.4° C. to 89.7° C after exposure for 100 hours. The thermal exposure stability was determined by measuring the clearing point of the mixture after heating at 150° C. for 100 hours in sealed melting-point capillaries (AB 3-2).The clearing point likewise dropped only slightly to 89.1° C. after heating. The measurement results are shown in Table IV.

TABLE IV

Clearing point of compound 4 in mixture B

| No. | UV exposure/h | Temperature exposure/h | Clearing point T (N,I)/° C. |
|---|---|---|---|
|  | 0 | 0 | 91.4 |
| AB 3-1 | 100 | 0 | 89.7 |
| AB 3-2 | 0 | 100 | 89.1 |

Use Example AB 4

The HTP of the novel compound 4 was investigated in mixtures C, D and E. The results are shown in Table V together with those from Use Examples AB 1-2 and AB 2-1.

TABLE V

HTP of compound 4 in various liquid-crystal mixture

| No. | Mix- ture | HTP (T)/$\mu$m$^{-1}$ | | | HTP (0° C.)/ HTP (50° C.) |
|---|---|---|---|---|---|
|  |  | T = 0° C. | T = 20° C. | T = 50° C. |  |
| AB 1-2 | A | −0.48 | −0.94 | −1.60 | 0.30 |
| AB 2-1 | B | −3.29 | −3.44 | −3.61 | 0.91 |
| AB 4-1 | C | −2.74 | −3.17 | −3.51 | 0.78 |
| AB 4-2 | D | −1.79 | −2.12 | −2.62 | 0.68 |
| AB 4-3 | E | −0.56 | −0.85 | −1.56 | 0.36 |

There is a correlation between the absolute value of the HTP and the temperature dependence of the HTP. At a low temperature dependence of the HTP, the absolute values of the HTP are large. Conversely, large temperature dependences of the HTP correlate with small absolute values of the HTP.

The characteristic voltages of the electro-optical characteristic lines of the liquid-crystal cells investigated are shown below by V (contr., θ, T), where contr. denotes the particular relative contrast in per cent, θ denotes the viewing angle in degrees in the preferred quadrant, and T denotes the temperature in degrees Celsius. The threshold of the electro-optical characteristic line for 10% relative contrast and perpendicular viewing is denoted below by $V_{10}$.

Use Example AB 5

The temperature dependence of the threshold voltage $V_{10}$ was measured for mixture J (AB 5-0) and for two different concentrations of the novel dopant 4 in mixture J (AB 5-1: mixture K=mixture J+0.5% by weight of compound 4; AB 5-2: mixture L=mixture J+1.0% by weight of compound 4). The results are shown in Figure I. Figure I shows that the dopant-free mixture J has a negative temperature dependence of the threshold voltage Vl, over the entire temperature range. The temperature dependence of the threshold voltage $V_{10}$ drops with rising concentration of the dopant in mixture J. It remains negative over the entire temperature range.

Use Example AB 6

Analogously to Use Example AB 5, the temperature dependence of the threshold voltage $V_{10}$ was measured for mixture E (AB 6-0) and, for comparison, for various concentration ratios of the dopants S-1011 and CB 15 known from the prior art in mixture E (AB 6-V1: mixture F=mixture E+0.14% by weight of S-1011+0.43% by weight of CB 15; AB 6-V2: mixture G=mixture E+0.23% by weight of S-1011+0.76% by weight of CB 15), and for various concentrations of the novel compound 4 in mixture E (AB 6-1: mixture H=Mixture E+1.0% by weight of compound 4; AB 6-2: mixture I=mixture E+1.5% by weight of compound 4). The results are shown in graph form in Figure II.

As can be seen from Figure II, mixture E has a highly negative temperature dependence of the threshold voltage $V_{10}$.

The addition of the dopants S-1011 and CB 15 known from the prior art to liquid-crystal mixture E results in a reduction in this temperature dependence, the resultant mixtures F and G likewise having a negative temperature dependence of the threshold voltage $V_{10}$ over the entire measurement range. The higher of the two overall concentrations of the known dopants used in Mixture G has a greater effect on the reduction of this temperature dependence. However, both mixtures F and G result in an increase in the threshold voltage $V_{10}$ at the low measurement temperature of −30° C. This increase is more pronounced in the case of mixture G, which has a higher concentration of dopant. However, The increase in the threshold voltage $V_{10}$ at −30° C. results in an undesired drop in the operating voltage. The increase in the threshold voltage $V_{10}$ at low temperatures is particularly undesired for battery-operated equipment, since, as is known, the terminal voltage of the batteries drops with temperature.

The novel compound 4 is particularly suitable for temperature compensation of the threshold voltage $V_{10}$ of mixture E. At the high measurement temperatures, it shows—depending on the concentration of novel compound in mixture E—a comparable (mixture H) or greater (mixture I) temperature compensation of the threshold voltage $V_{10}$ than the dopants known from the prior art (cf. Figure II, mixture F and mixture G). The novel mixtures H and I have the advantages over mixtures F and G that they reduce the threshold voltage $V_{10}$ at −30° C. and have a positive temperature dependence of the threshold voltage $V_{10}$ at the low measurement temperatures (See Figure II). These effects are more pronounced in the case of mixture I, which has a greater concentration of dopant.

Owing to the positive temperature dependence of the threshold voltage $V_{10}$ at low temperatures for the novel compound 4, it can be seen that the temperature compensation of the threshold voltage $V_{10}$ can be further augmented by mixing compound 4 with other dopants.

Use Example AB 7

A TN display having the following parameters:
Bias 1:3
Multiplex rate 1:4
and the requirement that it can be used without temperature compensation of the operating voltage $V_{op}$ was used to determine the temperature dependence of the characteristic voltage V (contr., θ, T). The values V(50, 10, T)$_{sel}$ for the selected state (requirement: minimum contrast of 50% at a viewing angle of 10°) and V(10, 45, T)$_{nonsel}$ for the non-selected state (requirement: maximum contrast of 10% at a viewing angle of 45°) are shown for mixture J in Figure III (AB 7-0) and for mixture M (=mixture J+1% by weight of compound 4) in Figure IV (AB 7-1). The improvement in the display properties through addition of the dopant to mixture J can be seen from the significant increase in the value for the operating tolerance (margin) for an only slight increase in the operating voltage $V_{op}$.

$$V_{op} = \frac{V(50, 10, -20)_{sel} + V(10, 45, +80)_{nonsel}}{2}$$

$$Margin = \frac{V(10, 45, +80)_{nonsel} - V(50, 10, -20)_{sel}}{2} \cdot \frac{100\%}{V_{op}}$$

The values for the operating voltage $V_{op}$ and the margin are shown in Table VI.

TABLE VI

Operating voltage and margin

| No. | Mixture | Operating voltage/V | Margin/% |
|---|---|---|---|
| AB 7-0 | J (dopant-free) | 4.65 | 5.6 |
| AB 7-1 | M (= mixture J + 1% by weight of compound 4) | 4.85 | 9.2 |

Use Example AB 8
An STN display having the parameters:

| | |
|---|---|
| Twist angle | 240° |
| Tilt angle | 5° |
| Layer thickness d | 6.19 μm |
| d · Δn | 0.85 |

(Δn: optical anisotropy)

was used to measure the temperature dependence of the threshold voltage $V_{10}$ of mixture N in which various concentrations of dopant are dissolved. The dopants used were the substance S-811 known from the prior art (AB 8-1: mixture O=Mixture N+0.73% by weight of S-811), the novel compound 4 (AB 8-2: mixture P=mixture N+3.29% by weight of compound 4; AB 8-3: mixture Q=mixture N+3.16% by weight of compound 4; AB 8-4: mixture R=mixture N+3.05% by weight of compound 4), and a combination of these two dopants (AB 8-5: mixture S=mixture N+0.36% by weight of S-811+1.65% by weight of compound 4). The values for the threshold voltage $V_{10}$ in the temperature range from −20° C. to +60° C. are shown in Table VII.

Table VII
Threshold voltage $V_{10}$ as a function of temperature for mixture N which includes various dopants in various concentrations Table VII shows that addition of the dopant S-811 known from the prior art does not compensate the temperature dependence of the threshold (mixture O has a negative temperature dependence of the threshold over the entire temperature range from −20° C. to +60° C.).

By contrast, the novel mixtures P and Q are highly suitable for temperature compensation of the threshold over the temperature range from −20° C. to +60° C. At the high temperature of +60° C., however, they exhibit the phenomenon of striped domains. This problem of striped domains can be substantially diminished with virtually constant temperature compensation of the threshold by reducing the dopant concentration (see AB 8-4).

Mixture S, which includes both dopant S-811 from the prior art and the novel dopant 4, shows, like mixture O, a negative—but much less pronounced—temperature dependence of the threshold in the temperature range investigated. By optimizing the concentrations of these dopants, very good temperature compensation of the threshold can be achieved between −20° C. and +20° C. This is evident from the negative temperature dependence of the threshold for dopant S-811 from the prior art (see AB 8-1) and the positive temperature dependence of the threshold for the novel dopant 4 in this temperature range (see AB 8-2 to AB 8-4).

What is claimed is:

1. A dopant compound of the formula I $$R^1\text{-}(A^1\text{-}Z^1)_n\text{-}A^2\text{-}W \qquad\qquad I$$

in which
W is

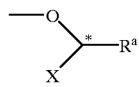

X is —C≡C—Y or —CH=CH—Y,
Y is
a) H or an alkyl or alkenyl radical having 1–15 carbon atoms which are unsubstituted, monosubstituted by CN or CF$_3$ or monosubstituted to perhalo-substituted by halogen, where one or more CH$_2$ groups in these radicals are optionally replaced, in each case independently of one another, by —O—, —CO— or —CO—O— in such a way that heteroatoms are not linked directly to one another, or
b) a phenylene radical in which one or two CH groups are optionally replaced by N and which is unsubstituted or

TABLE VII

Threshold voltage $V_{10}$ as a function of temperature
for mixture N which includes various dopants in various concentrations

| No. | Amount of dopant added to mixture N | d/p at 20° C. | Threshold voltage $V_{10}$ | | | | |
|---|---|---|---|---|---|---|---|
| | | | T = −20° C. | T = 0° C. | T = +20° C. | T = +40° C. | T = +60° C. |
| AB 8-1 | 0.73% S-811 | 0.53 | 1.41 | 1.35 | 1.30 | 1.24 | 1.17 |
| AB 8-2 | 3.29% of compound 4 | 0.53 | 1.26 | 1.29 | 1.31 | 1.31 | 1.27 |
| AB 8-3 | 3.16% of compound 4 | 0.51 | 1.26 | 1.28 | 1.30 | 1.29 | 1.25 |
| AB 8-4 | 3.05% of compound 4 | 0.49 | 1.26 | 1.28 | 1.28 | 1.26 | 1.22 |
| AB 8-5 | 0.36% S-811 + 1.65% of compound 4 | 0.53 | 1.34 | 1.32 | 1.30 | 1.27 | 1.23 | substituted one or more times by CN, Cl or F or by an alkyl, alkenyl or alkoxy radical having 1 to 8 carbon atoms, in which one or more H atoms are optionally replaced by F atoms, $R^a$ is a straight-chain alkyl radical having 1–15 carbon atoms $R^1$ is H or an alkyl or alkenyl radical having 1–15 carbon atoms which is unsubstituted, monosubstituted by CN or $CF_3$ or monosubstituted to perhalosubstituted by halogen, where one or more $CH_2$ groups in these radicals may optionally replaced, in each case independently of one another by —O—, —S—, —CO—, —CO—O—, —O—CO— or —O—CO— —O— in such a way that heteroatoms are not linked directly to one another, $A^1$ and $A^2$, in each case independently of one another, are a
  a) trans-1,4-cyclohexylene radical, in which one or more nonadjacent $CH_2$ groups are optionally replaced by —O— and/or —S—,
  b) 1,4-cyclohexenylene radical,
  c) 1,4-phenylene radical, in which one or two CH groups are optionally replaced by N,
  d) radical from the group consisting of 1,4-bicyclo[2.2.2]octylene, piperidine-1,4-diyl, naphthalene-2,6-diyl, decahydronaphthalene-2,6-diyl and 1,2,3,4-tetrahydronaphthalene-2,6-diyl, where the radicals a), b) and c) are optionally substituted by CN, Cl, F or an alkyl or alkenyl radical having 1 to 5 carbon atoms, $Z^1$ is —CO—O—, —O—CO—, —CH$_2$O—, —O—CH$_2$—, —CH$_2$CH$_2$, —CH═CH—, —C—C— or a single bond,
and
n is 0, 1, 2 or 3,
with the proviso that, in the case where $A^2$ is unsubstituted 1,4-phenylene and X is C≡CH, A¹is not 1,4-phenylene in which one or two CH groups are optionally replaced by N.

2. A dopant compound according to claim 1 of the formula I2

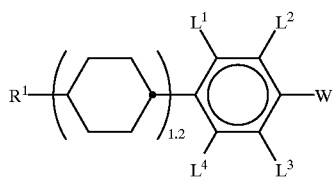

in which $R^1$ and W are as defined, and $L^1, L^2, L^3$ and $L^4$ are independently H, Cl or F.

3. A dopant according to claim 1 of the formula I6

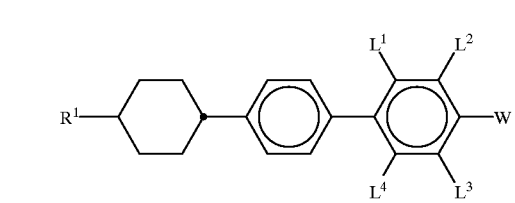

in which $R^1$ and W are as defined, and $L^1, L^2, L^3$ and $L^4$ are independently H, Cl or F.

4. A dopant compound according to claim 1, in which X is —C≡C—H, —CH═CH$_2$ or

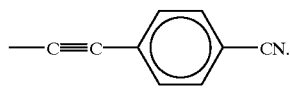

5. A dopant compound according to claim 1, in which W is of the formula (1)

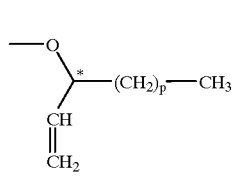

and p is 3, 4, 5, 6 or 7.

6. A dopant compound according to claim 1, in which W is of the formula (2)

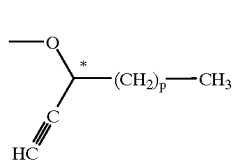

and p is 3, 4, 5, 6 or 7.

7. A dopant compound according to claim 1, in which W is of the formula (3)

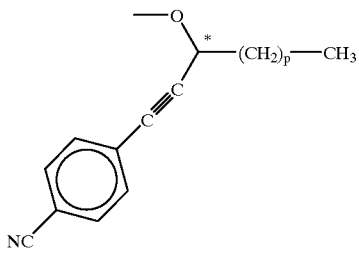

and p is 3, 4, 5, 6 or 7.

8. A liquid-crystalline medium, which comprises at least one dopant compound according to claim 1.

9. A liquid-crystalline medium according to claim 8, wherein the medium has a chiral tilted smectic phase.

10. A liquid-crystalline medium according to claim 8, wherein the dopant concentration is from 0.001% by weight to 40— by weight.

11. A liquid-crystalline medium according to claim 9, wherein the dopant concentratio is from 0.1% by weight to 40% by weight.

12. A liquid-crystalline medium according to claim 10, wherein the dopant concentration is from 0.001% by weight to 15% by weight.

13. An electro-optical display, which contains a liquid-crystalline medium according to claim 8.

14. A liquid crystalline medium according to claim 11, wherein, within the range of from 0° C. to 50° C., the cholesteric pitch of the medium has a temperature dependence of from 0.1% to 10% per °C.

15. A liquid crystalline medium according to claim 12, wherein, within the range of from 0° C to 50° C., the cholesteric pitch of the medium has a temperature dependence of from 0.1% to 10% per °C.

16. A liquid crystalline medium according to claim 8, wherein the medium has a temperature dependence of the threshold voltage of less than 0.1%/°C.

17. A liquid crystalline medium according to claim 8, wherein the medium has a temperature dependence of the threshold voltage of from 0.01%/°C. to 0.05%/°C.

* * * * *